United States Patent [19]

Hassouna

[11] Patent Number: 5,051,357
[45] Date of Patent: Sep. 24, 1991

[54] METHOD AND ASSAY USING INACTIVATION OF FACTORS VA AND VIIIA BY ACTIVATED PROTEIN C TO DIAGNOSE THROMBIC DISEASE OR ASSAY FOR PROTEIN C AND KIT THEREFOR

[75] Inventor: Houria I. Hassouna, Grosse Pointe, Mich.

[73] Assignee: Board of Trustees operating Michigan State University, East Lansing, Mich.

[21] Appl. No.: 396,234

[22] Filed: Aug. 21, 1989

Related U.S. Application Data

[63] Continuation-in-part of Ser. No. 379,988, Jul. 14, 1989.
[51] Int. Cl.$^5$ ............................................... C12Q 1/56
[52] U.S. Cl. ........................................ 435/13; 422/61; 436/69; 436/86
[58] Field of Search ............... 436/86, 69; 435/13; 422/61

[56] References Cited

U.S. PATENT DOCUMENTS 3,486,981 12/1969 Speck ........................... 436/69 X
4,705,756 11/1987 Spillert et al. ................ 436/69 X
4,908,314 3/1990 Orthner ........................ 435/13 X

FOREIGN PATENT DOCUMENTS 0182929 6/1986 European Pat. Off. ............. 435/13
0229234 7/1987 European Pat. Off. .
0260707 3/1988 European Pat. Off. .
3607559 9/1987 Fed. Rep. of Germany ........ 435/13

OTHER PUBLICATIONS

Martinoli et al, Chemical Abstracts, vol. 105, Abstract No. 105:93300x, 1986.
Kirk–Othmer vol. 4, pp. 1 to 24 (1978).

*Primary Examiner*—Robert J. Hill, Jr.
*Attorney, Agent, or Firm*—Ian C. McLeod

[57] ABSTRACT

A method and test kit for indirectly assaying for Protein C is described. The method uses tissue thrombomodulin/tissue factor (TTP) and calcium chloride to produce thrombin and activate Protein C to Protein Ca without fibrin formation and then allows time for Protein Ca to inactivate Factors Va and VIIIa. A deficient plasma has a decreased activated thromboplastin assay clotting time compared to a control plasma. The method and test kit is used to diagnose thrombic diseases.

24 Claims, 23 Drawing Sheets

☐ PT-BEFORE ACTIVATION
☒ PT-AFTER ACTIVATION
☐ PT-POST ACT., >5 MIN. INC

METHOD AND ASSAY USING INACTIVATION OF FACTORS VA AND VIIIA BY ACTIVATED PROTEIN C TO DIAGNOSE THROMBIC DISEASE OR ASSAY FOR PROTEIN C AND KIT THEREFOR

CROSS-REFERENCE TO RELATED APPLICATION

This application is a continuation-in-part of Ser. No. 379,988, filed July 14, 1989 now pending.

BACKGROUND OF THE INVENTION

The present invention relates to a method for diagnosing thrombic disorders by determining the inactivation of Factor Va and Factor VIIIa by activated Protein C (Protein Ca) in the plasma of a patient. In particular the present invention relates to an assay method which determines whether there is a deficiency of Protein C or whether there is increased inhibitor activity against Protein C in the plasma of the patient.

PRIOR ART

Protein C is the zymogen of a serine protease, Protein Ca. Protein Ca exerts an anticoagulant effect in plasma by the selective inactivation of non-enzymic activated cofactors FVa and FVIIIa. It has been shown by several investigators that the zymogen (inactivated) Factors V and VIII are poor substrates for Protein Ca. It has also been shown that on endothelial cell surfaces in blood, Protein C is activated to the protease by thrombin complexed with thrombomodulin. Thrombomodulin is an integral endothelial cell surface protein. A general discussion of blood Factors appears in Kirk-Othmer Vol 4, pages 1 to 24 (1978).

In vitro Protein C is slowly activated by thrombin alone or by thrombin/thrombomodulin at a much faster rate. Also Protein C is activated by purified Factor Xa and by Akistrodon Contortrix Contortrix (Southern Copperhead snake) venom. The component in the Akistrodon venom that is selective for the activation of Protein C has been purified and is given the trade name "PROTAC" TM. In addition to activating Protein C, Akistrodon Contortrix Contortrix (ACC) venom or the purified component in relatively large amounts (500 ng 20 ul) has been found to decrease, by direct proteolysis, the procoagulant activities of purified Factors II, VII, IX, X, and to cleave the A-alpha chain of fibrinogen. Thus, in vitro, ACC venom or the purified component exerts a broad substrate specificity.

Several assays to measure the biological activity of Protein C in plasma have been published. Some utilize lengthy and rather complicated experimental procedures that preclude their use in clinical diagnostic laboratories. Others use the purified Protein C activator from ACC venom to measure Protein C activity as a function of the prolongation of the APTT clotting times. The problem is that the zymogen (inactivated) Factors V and VIII are poor substrates for Protein Ca. Other assays are also described in European Patent Application Nos. 0,260,707 and 0,229,234.

OBJECTS

It is therefore an object of the present invention to provide an assay method for Protein C which is accurate and reliable and a test kit for performing the method. Further, it is an object of the present invention to provide a method which is simple and economical to perform and a test kit which is easy to use. These and other objects will become increasingly apparent by reference to the following description and the drawings.

GENERAL DESCRIPTION

Figure 1:
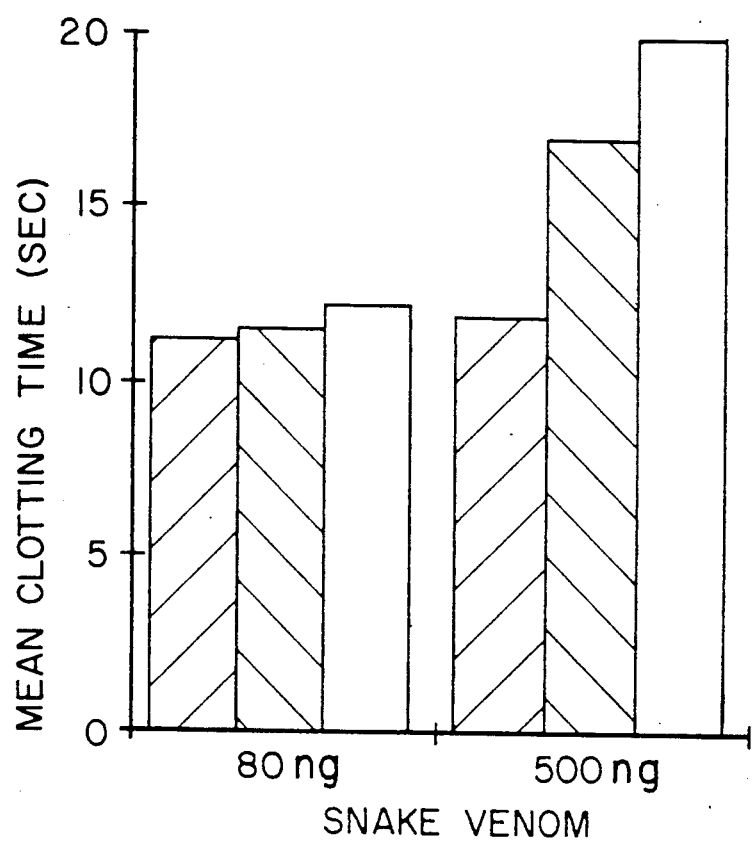
FIG. 1 is a graph showing the effect of 80 ng and 500 ng of ACC snake venom on the prothrombin time (PT) assay with PNP.

The present invention relates to a method for diagnosing a thrombic disease by testing for inactivation of Factors Va and VIIIa by activated Protein C (Protein Ca) which comprises: activating Factor V and Factor VIII to Factor Va and Factor VIIIa and activating Protein C to Protein Ca in a container of patient and pooled normal plasma (PNP) without fibrin formation in the plasmas; allowing time for Protein Ca to inactivate Factor Va and Factor VIIIa; and determining a clotting time of the patient plasma and the PNP in each container using an activated thromboplastin assay (APTT).

Further, the present invention relates to a method for indirectly assaying for Protein C in blood plasma which comprises: activating Factor V and Factor VIII to Factor Va and Factor VIIIa and activating Protein C to activated Protein C (Protein Ca); allowing time for Protein Ca to inactivate Factor Va and Factor VIIIa; and determining a clotting time of the patient plasma and the PNP in each container using an activated thromboplastin time assay (APTT) of the PNP and the patient plasma in each container, wherein a particular patient plasma with a deficiency of Protein C or with increased inhibitor activity against Protein Ca has a decreased APTT compared to the APTT of PNP.

Further still the present invention relates to a method for indirectly assaying for Protein C in blood plasma by activating Factor V to Factor Va and Factor VIII to Factor VIIIa and Protein C to activated Protein C (Protein Ca) in the plasma which comprises: providing separate containers of patient plasma and pooled normal plasma (PNP); adding thrombomodulin tissue factor (TTP) and calcium chloride to the plasmas in each container so as to activate Factor V to Factor Va, Factor VIII to Factor VIIIa and Protein C to Protein Ca without fibrin formation in the plasmas; allowing time for the Protein Ca to inactivate Factor Va and Factor VIIIa formed by the addition of TTP and calcium chloride to the plasmas; and determining a clotting time of the patient plasma and the PNP in each container using an activated thromboplastin assay (APTT), wherein a particular patient plasma with a deficiency of Protein C or increased inhibitor activity to Protein Ca has a decreased APTT compared to the APTT of PNP.

Finally the present invention relates to a kit for indirectly assaying for Protein C in blood plasma by a method which comprises providing in separate containers patient plasma and control pooled normal plasma (PNP); adding thrombomodulin/tissue factor (TTP) and calcium chloride to the plasmas in each container so as to activate Factor V to Factor Va and Factor VIII to Factor VIIIa Protein C to activated Protein C (Protein Ca) without fibrin formation in the plasmas; separately mixing Factor VIII and Factor V deficient plasma with the activated PNP and with the activated patient plasma in each of the containers; allowing time for Factor VIII and Factor V to be activated to Factor Va and Factor VIIIa and then to be inactivated by Protein Ca in the separate containers; and determining a clotting time of the patient plasma and the PNP in each container using an activated thromboplastin time assay (APTT), wherein a patient plasma with a deficiency of Protein C or with increased inhibitor activity against Protein Ca has a decreased APTT compared to the APTT of PNP which comprises: TTP with a standardized prothrombin time in PNP of between about 10 and 13 seconds to produce thrombin in a dosage amount of less than a dosage amount which produces fibrin formation in the PNP and the patient plasma; Factor V and Factor VIII and Protein C deficient plasmas; and an APTT reagent.

The present invention relates to an assay for the indirect measurement of the biological activity of Protein Ca by measurement of the inactivation of activated Factor V and Factor VIII in plasma. In the assay, pooled normal plasma (PNP) or patient plasma is activated by initiating thrombin formation via the extrinsic pathway. The amount of thrombomodulin tissue Factor/calcium chloride used in the assay to initiate thrombin formation in PNP does not lead to fibrin generation in the activated plasma. In PNP or in patient plasma, activation by thrombin of Factor V to Factor Va and FVIII to Factor VIIIa is measured by an APTT assay with Factor V and Factor VIII deficient plasmas. In the thrombin activated plasma, activation of Protein C to Protein Ca is aided by Akistrodon Contortrix Contortrix (ACC), a venom with recognized Protein C activating properties or by another Protein C activator. The amount of venom or other activator used in the assay does not cause prolongation of the APTT. Care must be taken not to use too much of the activator or of the thrombomodulin tissue factor/calcium chloride.

The standard assays using relatively large amounts of ACC to determine Protein C are inherently inaccurate. Studies during the development of the Protein C assay of the present invention have shown that when the amount of ACC added to 1 ml of plasma is greater than 100 ng/ml there is an immediate prolongation of the APTT, and when the amount of ACC is 500 ng/ml, there is an immediate prolongation of the PT as well as the APTT. This ACC dose dependent prolongation of the PT and APTT was examined using mixtures of PNP with several factor deficient plasmas (Factors II, V, VII, VIII, X and XII). There was a generalized decrease in activity for all the factors examined. These results seem to indicate broad specificity of ACC for various Factors, and are in agreement with the findings of Kiesel et al (Characterization of a Protein C Activator from Akistrodon Contortrix Contortrix Venom, J. Biol. Chem.: 262:12607–13, 1987). Another explanation for the dose dependent prolongation of the plasma clotting times with the generalized decrease in factor activities is that ACC venom interferes with the activation processes on negatively charged phospholipid surfaces in the manner of a lupus-like inhibitor.

Using the same experimental approach a protein C activating protease purified from ACC (PACC), was also examined for substrate specificity. When was added to plasma in the recommended dose (exactly as described by the manufacturer Diagnostica Stago) it prolonged the APTT clotting times. In a critical experiment, PACC activated plasma which was subsequently activated by Tissue Factor/CaCl$_2$ showed a shortening of the APTT. Factor Va and Factor VIIIa activities not only were not depleted, but were increased 11.5 fold and 29 fold over baseline. It is therefore highly likely that ACC and PACC induced prolongation of the APTT clotting times is via a lupus-like inhibitor mechanism.

In the Protein C assay of the present invention, standard curves for Protein C activity were constructed in three types of Protein C deficient plasmas, a commercially prepared reagent, a Protein C immunodepleted PNP, and plasma obtained from a 17 year old who attempted suicide by means of a coumarin derivative used for rat poisoning. The source of Protein C was PNP and the choice of Protein C activator was ACC.

The most striking finding of the present invention was that as little as 20% Protein Ca activity can destroy as much as 70% Factor V activity and 60% Factor VIIIa activity. This is in line with the work of Miletich et al (Absence of Thrombosis in subjects with Heterozygous Protein C Deficiency. NEJM 317:991-6, 1987).

When Protein Ca mediated inactivation of Factor V and Factor VIII was studied in patients who were administered therapeutic doses of heparin for thrombosis related problems so that Factor V and Factor VIII activities were very low. In a very recent publication (Antithrombin III-dependent Anti-prothrombinas Activity of Heparin and Heparin Fragments" Schoen P et al. J. Biol. Chem. 264:10002–7, 1989), Schoen et al hypothesize that the formation of the dissociable ternary ATIII-heparin-Factor Xa complex results in a (partial) loss of Factor Xa activity towards its natural substrate prothrombin. Thus the activation of Factor V and Factor VIII is decreased in heparinized plasma as a result of a decrease in the initial rate of thrombin generation in the presence of ATIII.

Also studied was Factor V and Factor VIII activation and inactivation in the case of a 33 year old patient on continuous heparin therapy for almost three years with spontaneous recurrent deep vein thrombosis (DVT) and cavenous sinus thrombosis while on heparin. In this patient, Factor Va and Factor VIIIa activity remained high and was not inactivated by Protein Ca. However, Protein C immunoreactive levels as well as Protein C purified from the patient's plasma were found in Dr. Miletich's laboratory to be normal. An explanation for the persistence of activated Factor V and Factor VIII in plasma and the recurrence of thrombosis while on heparin therapy is explained in a recent publication. Pratt et al purified Protein C inhibitor and studied the effect of heparin on purified Protein C inhibitor interaction with proteases. A heparin-dependent inhibition of activated Protein C was demonstrated that indicates a "procoagulant effect of heparin" mediated via Protein C inhibitor. (Protein C inhibitor: Purification and Proteinase Reactivity, Pratt C. W. et al Thrombos Res. 53: 595–602, 1989).

The mechanism for thrombosis in heparinized patients could, therefore, be the result of circulating activated Factor V and Factor VIII procoagulant activities. Under challenge to the hemostatic system such as a decrease in the blood flow, activated Factor V and Factor VIII would increase the initial rate of thrombin generation. Thus, the hypothesis of an immediate irreversible heparin-dependent inactivation of the 33 year old patient's Protein Ca could be the likely cause of his recurrent thrombotic problems that started at age 23.

An assay that measures the activation and inactivation of Factor V and Factor VIII in plasma is a sensitive indicator for hypercoagulability and reflects an imbalance of more than just the Protein C inhibitor pathway.

Poisonous Snake venom is preferred and Akistrodon Contortrix Contortrix (ACC) venom is most preferred. Purified fractions such as PACC can be used; however, they are not preferred for cost reasons. Also thrombomodulin and thrombin can be used to activate Protein C without fibrin formation; however, they are not preferred.

SPECIFIC DESCRIPTION

In Comparative Example I hereinafter, the major issue of substrate specificity in plasma for the ACC venom and its Protein C activating component, PACC, is addressed. Very strong evidence is presented for broad substrate specificity or lupus-like inhibitor activity.

In Example II hereinafter, the assay for Protein C is specifically described. Biological activity of Protein Ca is measured as a function of percent change in Factor V and Factor VIII activity.

A. Principle of the Protein C Assay

1. Plasma was activated to provide Factors Va, VIIIa and Ca by thrombomodulin/tissue Factor and calcium chloride. The amount of tissue Factor and calcium chloride solution that activates plasma was carefully calculated. As little as 20 ul of commercial Thromboplastin/-$CaCl_2$ 0.02M solution activated PNP. Evidence for generation of thrombin in the activated plasma is obtained by an increase in Factor Va and Factor VIIIa activity without detectable fibrin formation. The maximum amount of Thromboplastin/$CaCl_2$ 0.02M solution that fully activates PNP without detectable fibrin formation is 50 ul.

To prepare a suitable commercial Thromboplastin/-$CaCl_2$ 0.02M solution that will activate plasma at the recommended 20 ul to 50 ul range, distilled water is added to the dried powder to give in a fibrometer a clotting time by the PT assay for PNP of 11.6 seconds ($\mp 0.5$).

2. Measurement of Activated Factors V and VIII by the APTT assay. 30 ul plasma before activation and 30 ul plasma after activation are each added to 70 ul Factor V and Factor VIII deficient plasma. Measurement of change in activity is by the change in the clotting time by the APTT assay.

3. Protein C is preferably also activated by 80 to 100 ng of ACC venom. The proteolytic activity of snake venom used, 80 to 100 ng, is selective for Protein C. The activation of Protein C by ACC venom is used to speed the activation process that is started by thrombin. Thrombin formation is initiated in plasma by thromboplastin/calcium chloride solution as described above. If the snake venom step is omitted, a time interval of one hour is necessary for the inactivation of Factors Va and Factors VIIIa by thrombin activated Protein Ca.

B. Biological Activity of Protein Ca is measured as a function of percent change in Factor V and Factor VIII activity. At the end of one hour incubation, 30 ul of plasma mixture are added to 70 ul of Factor V and Factor VIII deficient plasma. Factor activity is determined from clotting times by means of standard curves. Protein C activity is calculated from the change in Factor Va and Factor VIIIa activity.

MATERIALS AND REAGENTS

Preparation of Pooled Normal Plasma (PNP)

Human pooled normal plasma (PNP) was prepared from forty healthy blood donors ranging in age from 18 to 64 years. Blood (4.5 ml) was drawn from each donor into vacutainer tubes each containing 0.5 ml of 3.85% acidified sodium citrate solution. Blood was spun at 2,000 r.p.m. in a refrigerated Beckman table top centrifuge at 2° C. for 10 to 15 minutes. The platelet poor plasma was pooled into a polystyrene beaker placed on ice, and then assayed for procoagulant factor levels by the PT and APTT assays. Fibrinogen levels were determined by clotting and chemical assays. One milliliter aliquots of PNP were then pipetted into 4 ml polystyrene capped tubes and stored at −80° C. for use in the Protein C experiments.

Akistrodon Contortrix Contortrix (Southern Copperhead Snake; ACC) Venom

One gram of freeze dried ACC venom powder was purchased from Sigma Chemical Company of St. Louis, Mo. Twenty samples of dried powder of 0.1 mg each were weighed and stored in 15 ml graduated capped plastic centrifuge tubes at 4° C. until further use. The dried venom was dissolved in distilled water (0.1 mg/10 ml) and assayed for stability by adding 500 ng ACC venom to 1 ml PNP. The proteolytic anticoagulant activity was tested by the APTT assay. The proteolytic anticoagulant activity was markedly decreased within 24 hours after reconstitution in distilled water. Proteolytic anticoagulant activity was, though, retained in the dried powder. Fresh solutions therefore were prepared daily by adding 10 ml distilled water to the graduated plastic centrifuge tubes containing 0.1 mg of dried powder. Venom solutions were kept on ice for the duration of the experiments.

Two concentrations of the venom, 80 ng and 500 ng per milliliter PNP, were tested for substrate selectivity by PT, APTT and Thrombin Clotting Time (TCT) assays.

Tissue Thromboplastin Reagents

Two reagents from the same manufacturer were used. The Tissue Thromboplastin/Calcium Chloride Powder (TTP/$CaCl_2$) was purchased from Ortho Diagnostic Systems Inc., Raritan, N.J. The Ortho Brain thromboplastin ISI Standard lot 871007 was obtained from Ortho Diagnostics Systems.

The commercially prepared tissue thromboplastin/calcium chloride powder was reconstituted to give a prothrombin time on a fibrometer of 11.6±0.5 seconds on 100 ul PNP. These reagents have high thrombomodulin activity (Thrombos Res 43:265-274 (1986)).

Activated Partial Thromboplastin (APTT) Reagent

Thrombosil TM I, a commercially prepared brain cephalin with silica activator, was purchased from Ortho Diagnostic Systems.

Calcium Chloride Reagent - 0.02 molar solution

Thrombofax TM, a bovine brain cephalin solution was also purchased from Ortho Diagnostic Systems.

Human Alpha Thrombin with a specific activity of 3,000 units/ug was obtained from an independent source. Clotting activity of the thrombin in 0.1M $CaCl_2$ solutions is retained for several years. A preservative, Thimerosal TM, purchased from Sigma Chemical Company, is added to the thrombin solutions at 1 mg/100,000 ml. Thrombin solutions of 1.5 to 1.2 unit per 100 ul 0.1M $CaCl_2$ were prepared to give a clotting time of 8-10 seconds with 200 ul PNP.

Equipment

A Dataclot TM 2 fibrometer from Helena Laboratoraies, Beaumont, Tex. was used for the clotting experiments. An Apple TM MacIntosh Computer and an IBM TM PC were used for the analysis and graphing of the data.

EXPERIMENTAL PROCEDURES

Prothrombin Time (PT) Assay

PNP or plasma mixtures (100 ul) were clotted with 200 ul TTP/$CaCl_2$ solution. The clotting times were recorded on a fibrometer.

Activated Partial Thromboplastin Time (APTT) Assay

PNP or plasma mixtures (100 ul) were incubated with APTT reagent for 3 to 5 minutes then clotted with 100 ul $CaCl_2$ 0.02M.

Thrombin Clotting Time (TCT) Assay 200 ul PNP or plasma mixtures were clotted with 100 ul thrombin solution (1.5 to 1.2 unit)

Single Factor Genetically Deficient Plasma Reagents (less than 1% activity)

Factor XI deficient reagent was purchased from George King, Biomedical, Inc., Overland Park, Kans. All other factor deficient plasmas were obtained by plasmapheresis from patients at the Michigan State University Medical Center.

Standard Curves for Factors V, VII, VIII, IX, X, XI, and XII

Standard curves were constructed using single factor genetically deficient plasmas and PNP. The clotting times by PT and APTT assays for about forty estimates per point were analyzed. Standard deviation, linear regression, Pearson's correlation coefficient, as well as mean and median were calculated for each curve.

In Table I the clotting times by PT for Factors V, VII and X activities ranging from 80% to less than 1% are presented.

TABLE I

Standard curves for descending ranges of Factors V, VII and X activities and the mean clotting times obtained by PT assay.
A least squares linear regression of the actual data points from the straight lines of the best fit are shown in this figure. Factor activities and the corresponding clotting times that represent the critical threshold procoagulant Factor V, VII or X levels whereby spontaneous bleeding can occur are placed in boxes.
Comparison of Data for the Mean Clotting Times by the PT Assay for Descending Ranges of Factors V, VII, and X Procoagulant Activities (40% to less than 1%)

| % Factor Activity | FV | FVII | FX |
|---|---|---|---|
| | (Clotting Time in Seconds) | | |
| 40 | 13.08 | 12.78 | 12.81 |
| 35 | 13.66 | 12.97 | 13.29 |
| 30 | 14.25 | 12.16 | 13.77 |
| 25 | 14.83 | 13.35 | 14.26 |
| 20 | 15.54 | 13.89 | 15.09 |
| 16 | 16.78 | 14.71 | 16.61 |
| 15 | 17.09 | 14.92 | 16.98 |
| 12 | 18.02 | 15.54 | 18.12 |
| 8 | 19.25 | 16.36 | 19.63 |
| 4 | 20.49 | 17.19 | 21.14 |
| 3 | 25.13 | 18.43 | 26.13 |
| 2 | 31.55 | 20.79 | 32.51 |
| 1.5 | 34.76 | 22.02 | 35.69 |
| 1 | 37.97 | 23.25 | 38.88 |
| 0.5 | 41.18 | 24.47 | 42.07 |
| 0 | 44.39 | 25.70 | 45.26 |

In Table II the data presented are the clotting times by the APTT assay for Factors V, VIII, IX, X, and XI activities ranging from 80% to less than 1%.

TABLE II

Standard curves for descending ranges of Factors V, VIII, IX, X and XI activities and the mean clotting times obtained by the APTT assay. A least squares linear regression of the actual data points from the straight lines of the best fit are shown in this figure. Factor activities and the corresponding clotting that represent the critical threshold procoagulant Factor V, VIII, IX, X or XI activities whereby spontaneous. Comparison of Data for the Mean Clotting Times by the APTT Assay for Descending Ranges of Factors V, VIII, IX and XI Procoagulant Activities (40% to less than 1%)

| % Factor Activity | FV | FVIII | FIX | FX | FXI |
|---|---|---|---|---|---|
| | | | Clotting Time in Seconds | | |
| 40 | 30.38 | 28.97 | 30.12 | 31.53 | 33.80 |
| 35 | 31.73 | 30.16 | 30.61 | 32.18 | 34.77 |
| 30 | 33.08 | 31.35 | 21.10 | 32.83 | 35.73 |
| 25 | 34.43 | 32.54 | 31.58 | 33.48 | 36.68 |
| 20 | 35.78 | 33.73 | 32.06 | | 37.63 |
| 16 | 36.86 | 34.69 | | | |
| 16 | 37.1 | 33.74 | 33.56 | 36.34 | |
| 12 | 42.4 | 37.97 | 35.93 | 39.13 | |
| 8 | 47.7 | 42.20 | 38.30 | 41.91 | 44.59 |
| 4 | 53.0 | 46.42 | 40.67 | 44.70 | 53.29 |
| 2 | | 48.54 | | | 57.65 |
| 2 | 65.75 | 47.54 | 45.11 | 47.42 | |
| 1.5 | 77.44 | 55.61 | 47.76 | 52.32 | 70.95 |
| 1 | 89.14 | 63.68 | 50.40 | 57.23 | |
| 0.5 | 100.84 | 71.75 | 53.04 | 62.13 | 88.51 |
| 0 | 112.54 | 79.82 | 78.54 | 67.03 | 97.29 |

Factor Assays

In the Protein C assay experiments, most of the Factor assays were performed by PT or APTT assay after adding 30 ul plasma mixtures to 70 ul single factor deficient plasma (Factors V, VII, VIII, IX, X, XI or XII) and recording the mean clotting times. The mean clotting time was never from less than four estimates with an average of ten estimates per point. Factor activities were then derived from the corresponding clotting times on the linear regression of the standard curves.

Activation of Plasma

One milliliter of PNP or patient plasma was activated by adding 50 ul, 30 ul, 20 ul or 10 ul solutions of TTP/CaCl$_2$. The tube was gently shaken and incubated at 37° C. for times ranging from zero to one hour. PT, APTT, TCT, and Factor assays were performed on activated plasma and on plasma prior to activation.

Standard Curves for Protein C

Three standard curves for Protein C were constructed on:

1) Protein C freeze dried deficient plasma reagent purchased from Diagnostica Stago, Asniere, France.

2) Plasma obtained from a 16 year-old patient who attempted to commit suicide by ingestion of three packages of a long lasting coumarin derivative prepared commercially and for use as a rat poison (trade name: Enforce ™). The patient's PT was 72 secs. (control 11.2 secs.), APTT 132.4 secs. (control 26.4 secs.) and TCT 9.9 secs. (control 9.2 secs.). Factor VII activity in this patient's plasma was less than 1%, Factor X activity 2%, and FIX activity 2.5%.

3. PNP immunodepleted of Protein C by anti-Protein C insolublized rabbit immunoglobulins.

Human anti Protein C antibodies were purchased from Diagnostica Stago, Asnieres, France. Coupling of the anti-Protein C antibodies to sepharose beads and immunodepletion of PNP by insolublized antibodies was performed as described by H. I. Hassouna and J. A. Penner. Antibody Techniques and Blood Coagulation. Sem Thromb Haemost (E. F. Mammen, ed) Vol 7, No 2, pp 61-111, (1981).

COMPARATIVE EXAMPLE I

Substrate Specificity for Akistrodon Contortrix Contortrix venom (ACC) and Its Purified Protein C Activating Protease "PROTAC"

Two concentrations of Akistrodon Contortrix Contortrix (ACC) venom were tested for effect on the clotting times of PNP by PT assay. In the experiment 80 ng and 500 ng ACC venom solutions in distilled water (20 ul) were added to 1 ml plasma. A prolongation of the PT was observed immediately after activation of plasma with 500 ng/20 ul ACC venom in distilled water. The mean clotting time of PNP (11.2 secs) was prolonged 1½ times immediately after adding the venom and 2 times after a 5 minute incubation period as shown in FIG. 1. No effect was observed when 80 ng ACC venom was added to plasma even after an incubation period greater than 5 minutes at 37° C. (FIG. 1).

Figure 2:
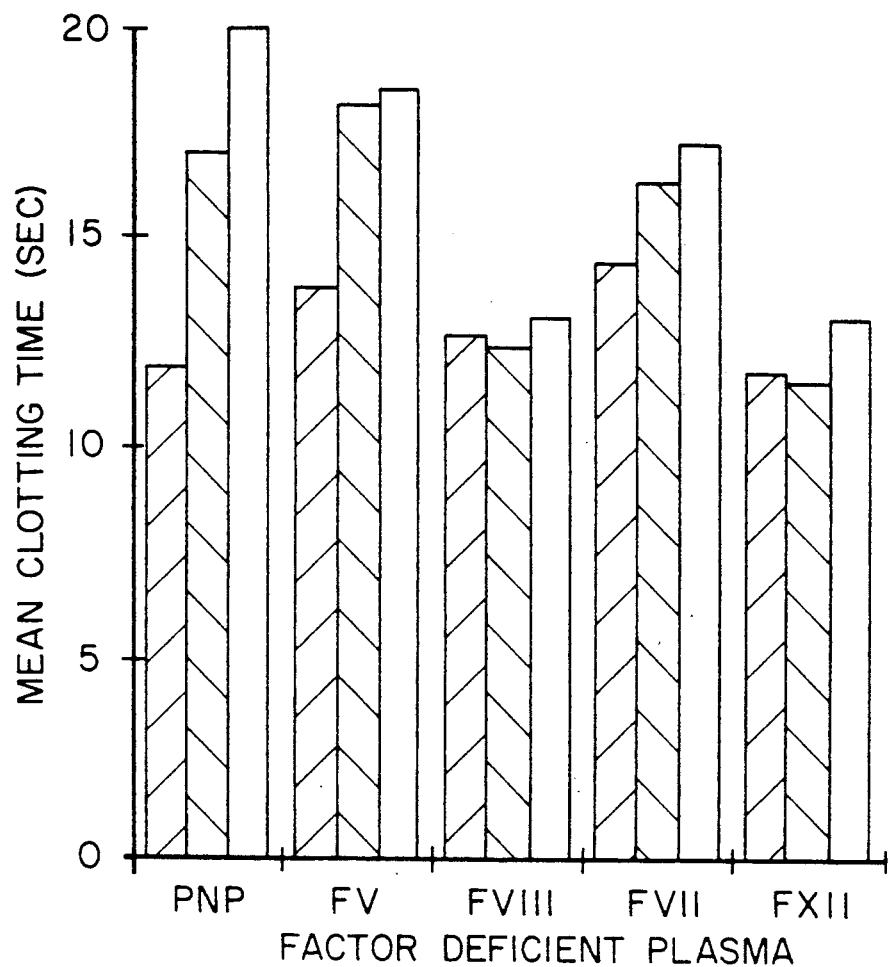
FIG. 2 is a graph showing PNP and shows the effect of 500 ng of ACC snake venom on various factor deficient plasmas in the PT assay. Two concentrations of snake venom were tested for effect on the clotting times of PNP by PT assay. In the experiment 80 ng and 500 ng snake venom solutions in distilled water (20 ul) were added to 1 ml plasma. A prolongation of PT was observed immediately after activation of plasma with a 500 ng/20 ul solution of snake venom in distilled water. The mean clotting time of PNP of 11.2 secs was prolonged 1½ times immediately after adding the venom and 2 times after a 5 min incubation period.
Figure 3:
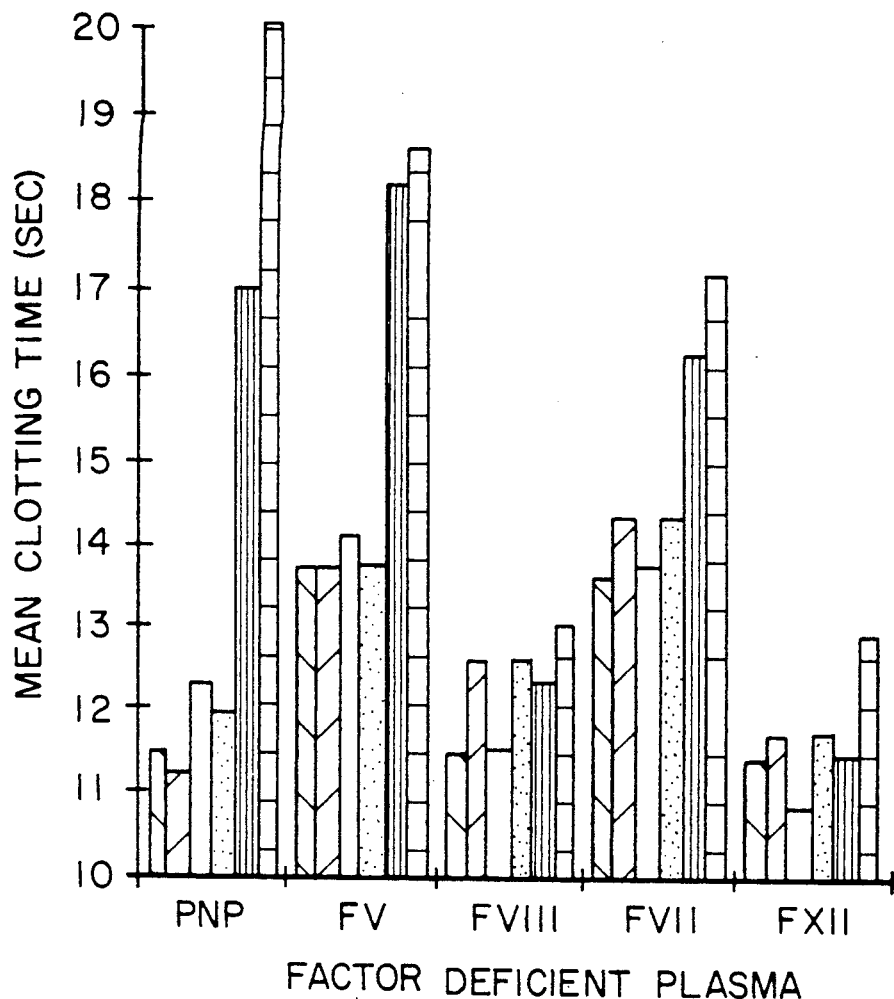
FIGS. 3 and FIGS. 4A, 4B and 4C are graphs showing the effect of 500 ng of ACC snake venom on the PT assay on a side by side basis for various factor deficient plasmas.
Figure 4A:
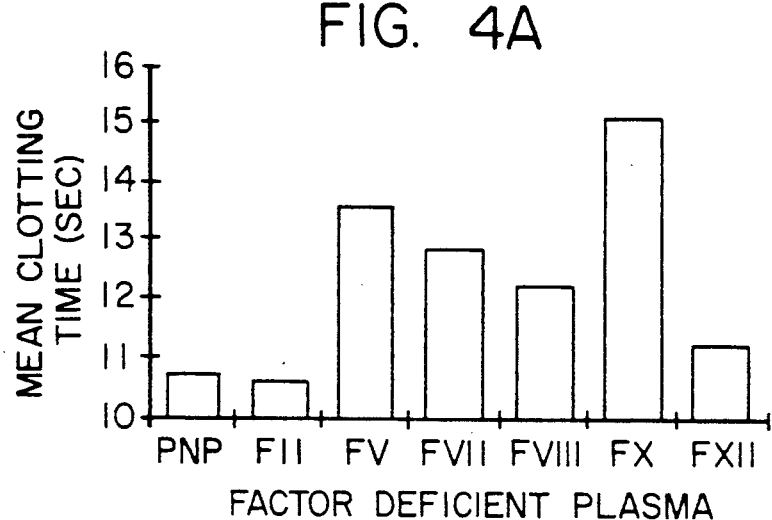
Figure 4B:
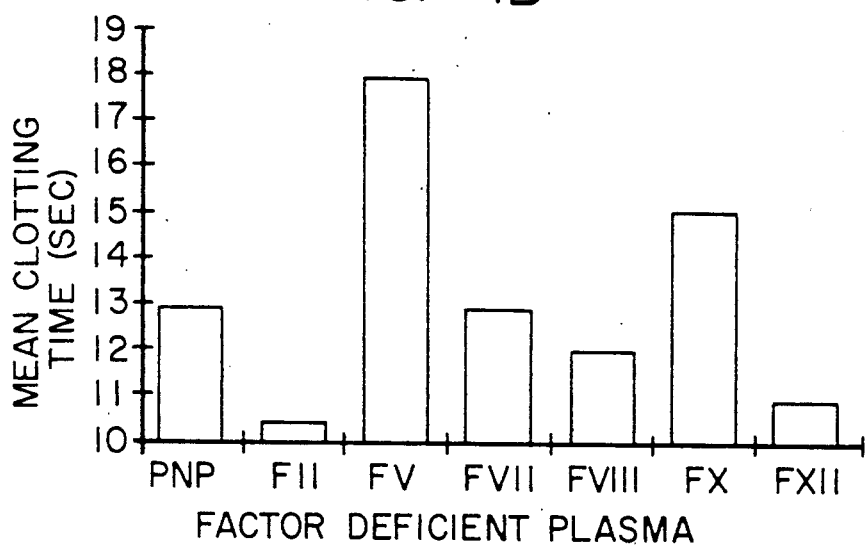
Figure 4C:
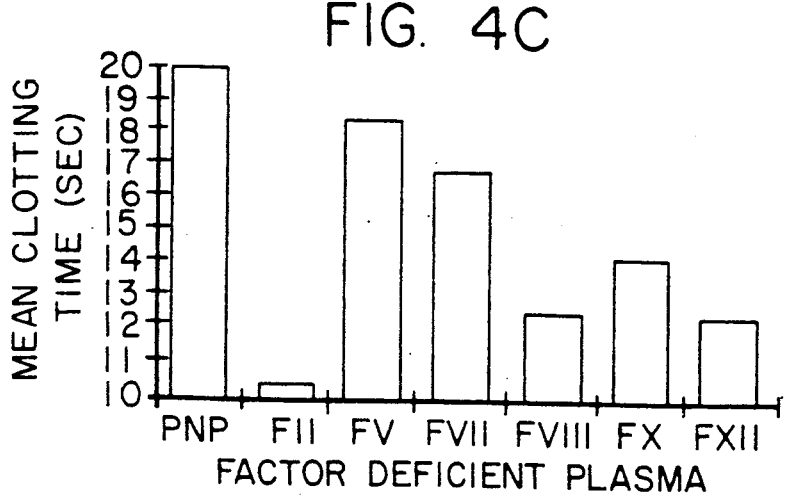
Figure 5:
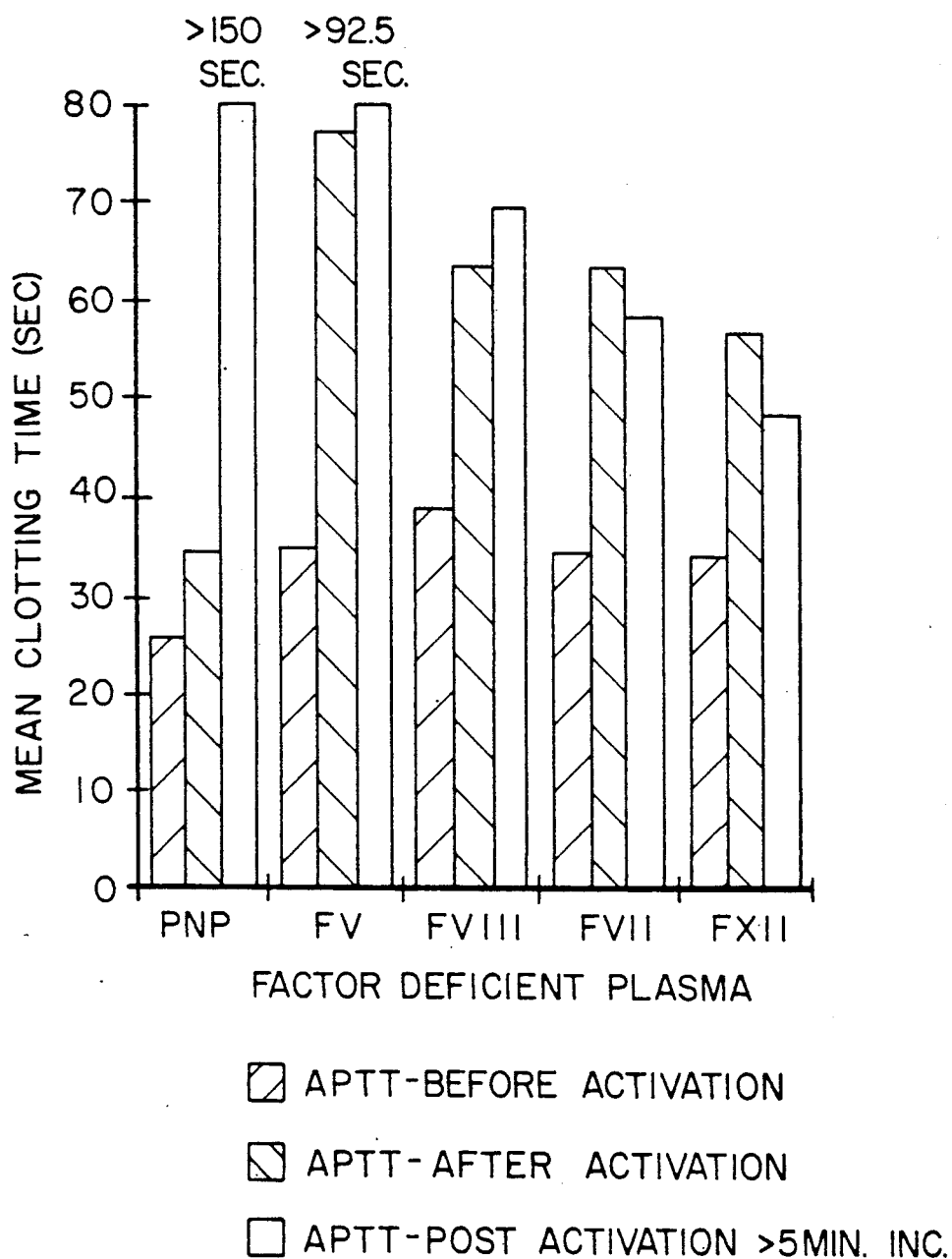
FIG. 5 is a graph showing the effect on the APTT assay of 500 ng ACC snake venom for PNP and various Factor deficient plasmas.
Figure 6:
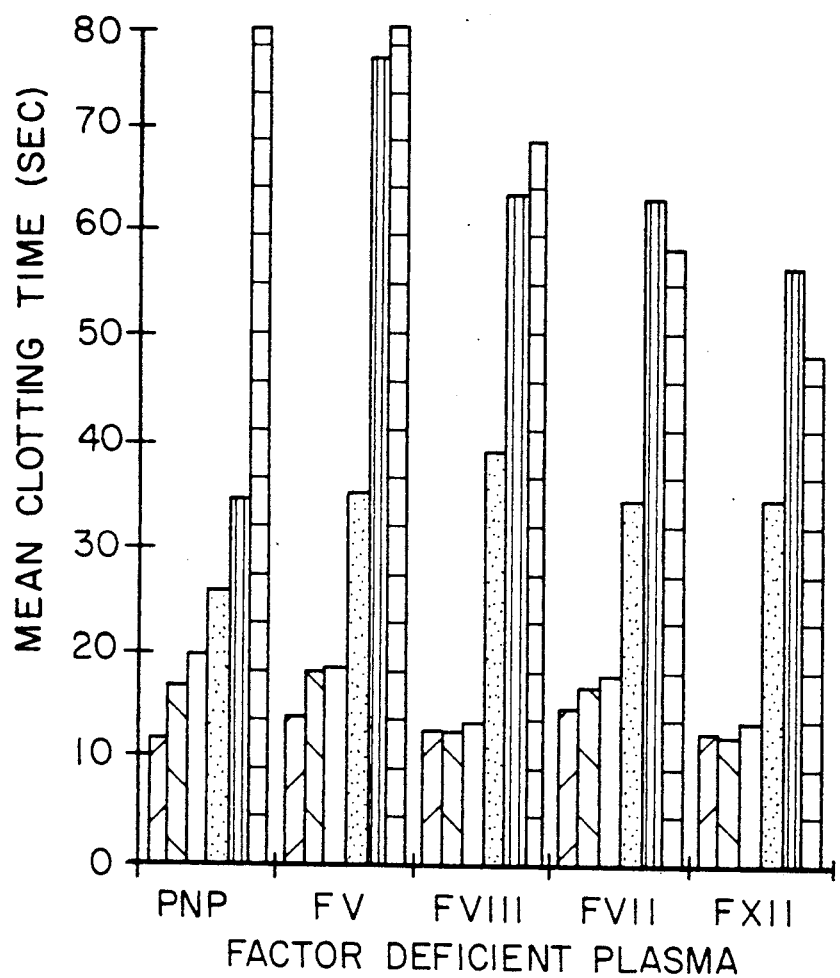
FIG. 6 is a graph comparing the PT and APTT assays with 500 ng of ACC snake venom.

To determine what effect the proteolytic activity of the ACC venom (500 ng) had on coagulation factors in plasma, 30 ul of plasma activated by ACC venom was added to 70 ul of factor deficient plasma (Factors V, VII, VIII, and XII). No change in clotting times was observed with Factor VIII or Factor XII deficient plasmas after activation with the venom. A prolongation of the PT was seen with Factor V and Factor VII deficient plasmas (FIG. 2). In FIGS. 3 and 4, the effect of 500 ng ACC venom on the clotting times of PNP by the PT assay is compared side by side with the effect of 500 ng ACC venom on selected factors (these findings were presented separately in FIG. 1 and FIG. 2). As can be seen in FIG. 5, the effect of 500 ng ACC venom on PNP and on coagulation Factors V, VII, VIII, and XII by APTT is more pronounced and nonselective. In FIG. 6, the effect of 500 ng ACC venom on PNP and Factors V, VII, VIII, and XII by the PT and APTT assays is presented for comparison.

Figure 7:
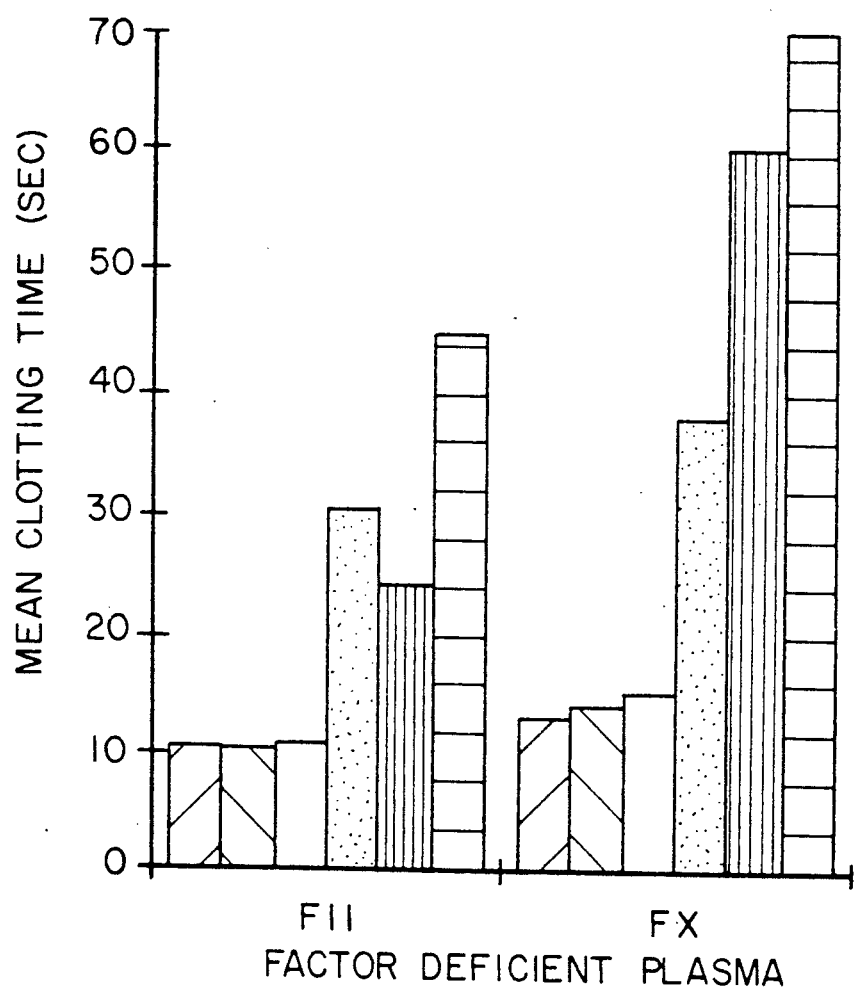
FIG. 7 is a graph showing the effect on the PT and APTT assays of 500 ng of ACC snake venom on Factor X and prothrombin (Factor II).
Figure 8:
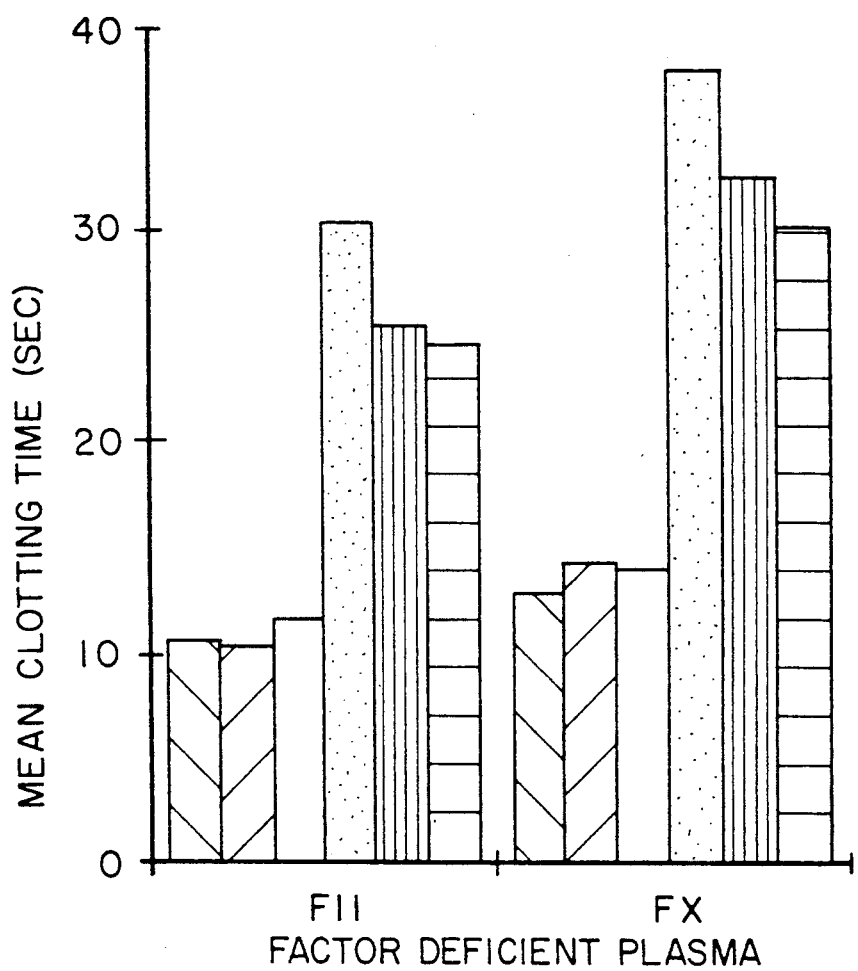
FIG. 8 is a graph showing the effect on the PT and APTT assays of 80 ng of ACC snake venom on Factors II and X.

To determine whether the proteolytic activity of the venom is directed at Factor X and prothrombin, the same experimental protocol using Factor II and Factor X deficient plasmas was performed. As can be seen in FIG. 7, there is a marked prolongation of the APTT in Factor X deficient plasma indicating possible inactivation of Factor X by the venom. A time dependent inactivation of prothrombin is observed, though it is modest compared to the substantial decrease in Factor X activity. When the amount of ACC venom used was 80 ng, there was no apparent inactivation of any of the coagulation factors examined (FIG. 8). From these results, it appears likely that, at the concentration of 500 ng ACC venom per ml PNP used in the experiments, the proteolytic specificity of the venom is broad. This is in agreement with previously published work by Keisel, et al (Characterization of a Protein C Activator from Akistrodon Contortrix Contortrix Venom, J. Bio. Chem., 262 p. 12607-13, (1987)).

Another possibility, even more probable, is that in plasma, ACC venom interferes with the activation processes on negatively charged phospholipid surfaces and behaves in the manner of a lupus-like inhibitor. Regardless of the mode of action of the venom, whether by direct proteolysis or by preventing complex assembly on negatively charged phospholipids, it is obvious that at the 50 ng concentration of ACC venom used in the experiments, the prolongation of the APTT is not by Protein Ca mediated inactivation of Factors VA and VIIIa and thus the prior art assays are not measuring Protein C.

Figure 9:
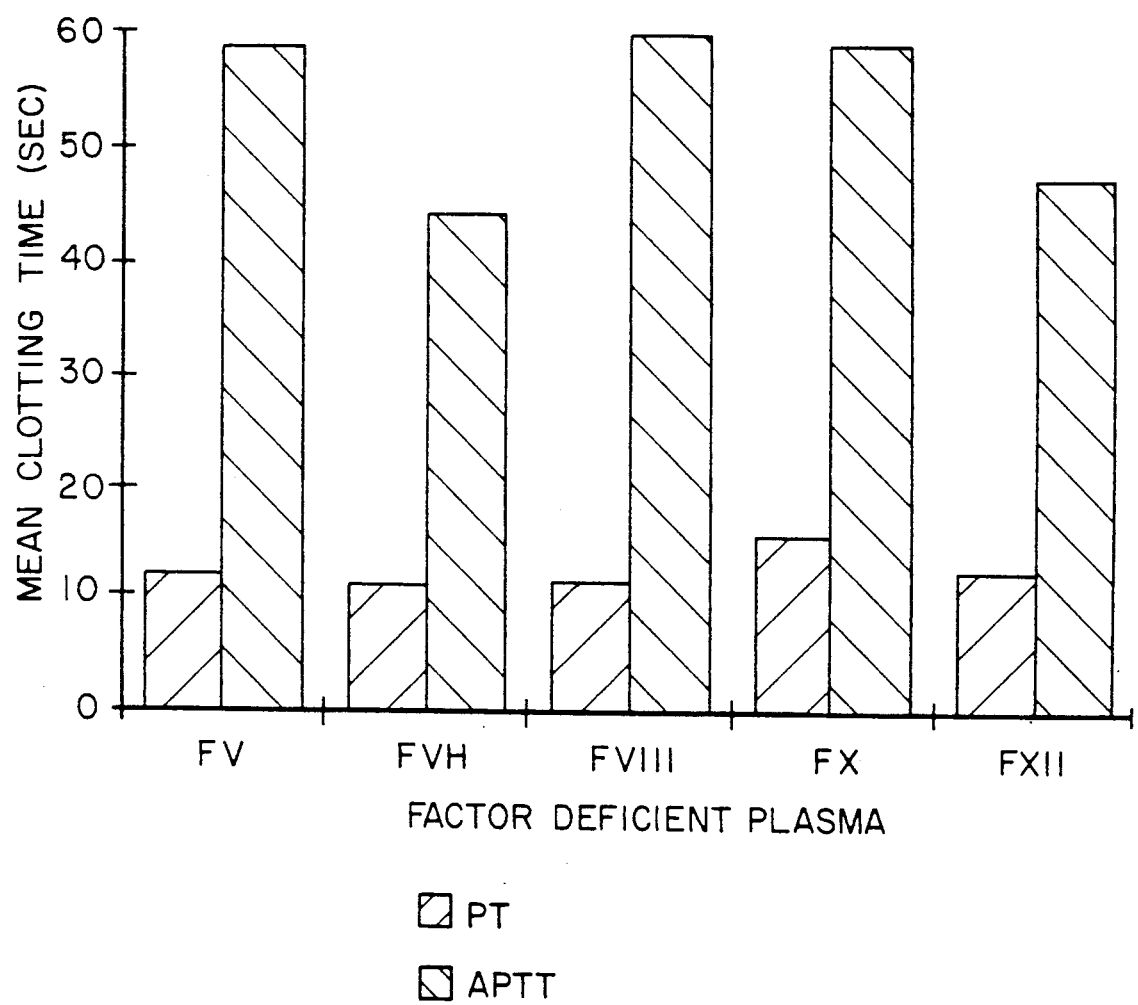
FIG. 9 is a graph showing the effect of an ACC snake venom derivative on the PT and APTT assays for selected Factor deficient plasmas.
Figure 10:
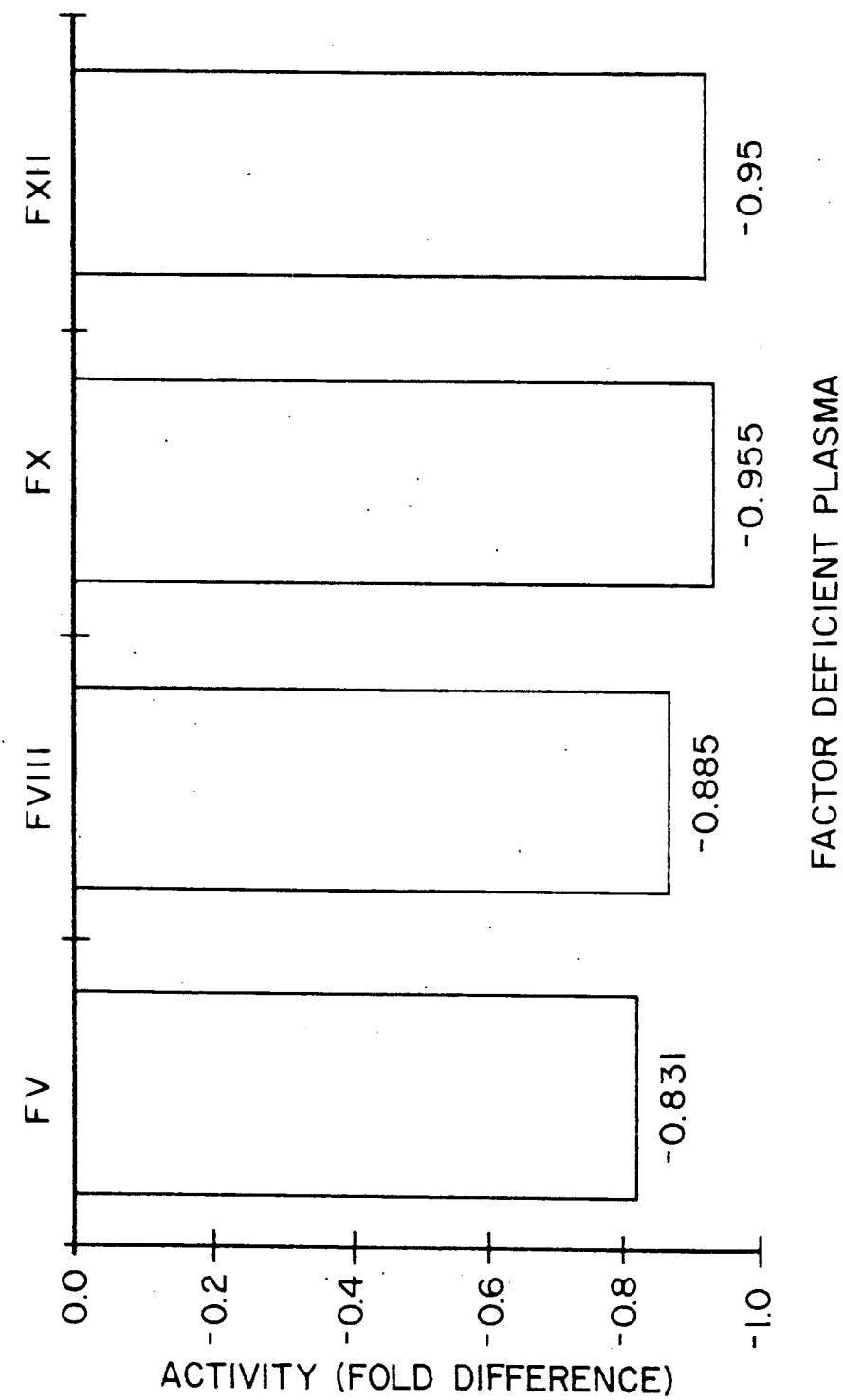
FIG. 10 is a graph showing the effect on the APTT assay of the ACC derivative on other factors in the APTT assay.

To examine the substrate specificity of PACC, it was added to PNP in the same enzyme or substrate ratio as recommended by the manufacturer. PNP (1 ml) was added to 1 vial of PACC. 30 ul of the plasma mixture was immediately tested by APTT in 70 ul each of Factor V, VIII, X, and XII deficient plasma. A decrease in Factor V activity from 16-20% to 3% was observed. For Factor VIII, a very similar decrease in activity from 16-20% to 1% was obtained; Factor X activity decreased from 20-25% to 1% and FXII activity from 40 to 4% (FIG. 9). In FIG. 10, the results of the activity measurements for Factors V, VIII, X and XII by PAC are expressed as fold changes in activity from initial factor activity measured in 30 ul PNP.

Figure 11:
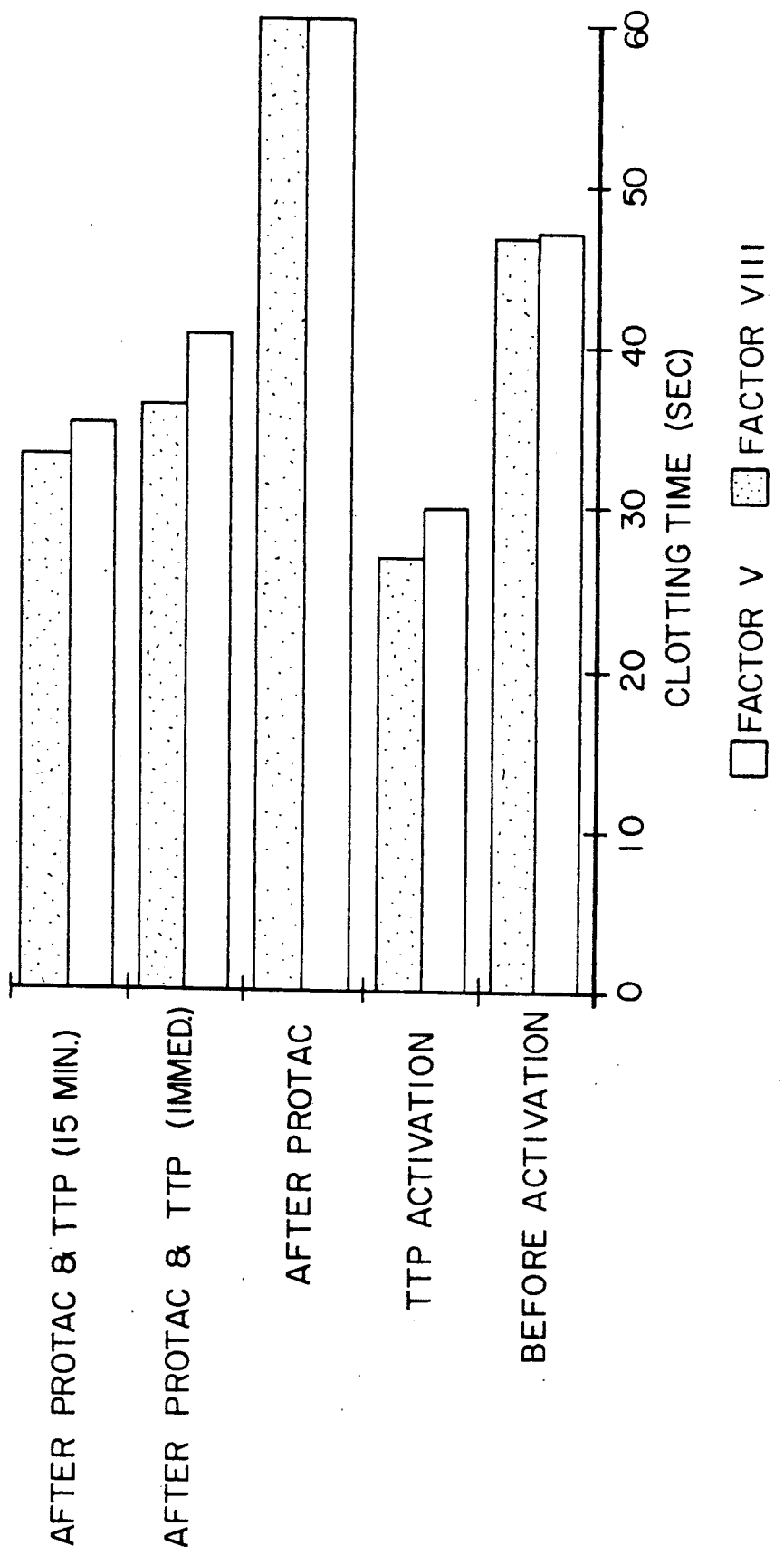
FIGS. 11 and 12 are graphs showing the results of the ACC derivative on the APTT assay.
Figure 12:
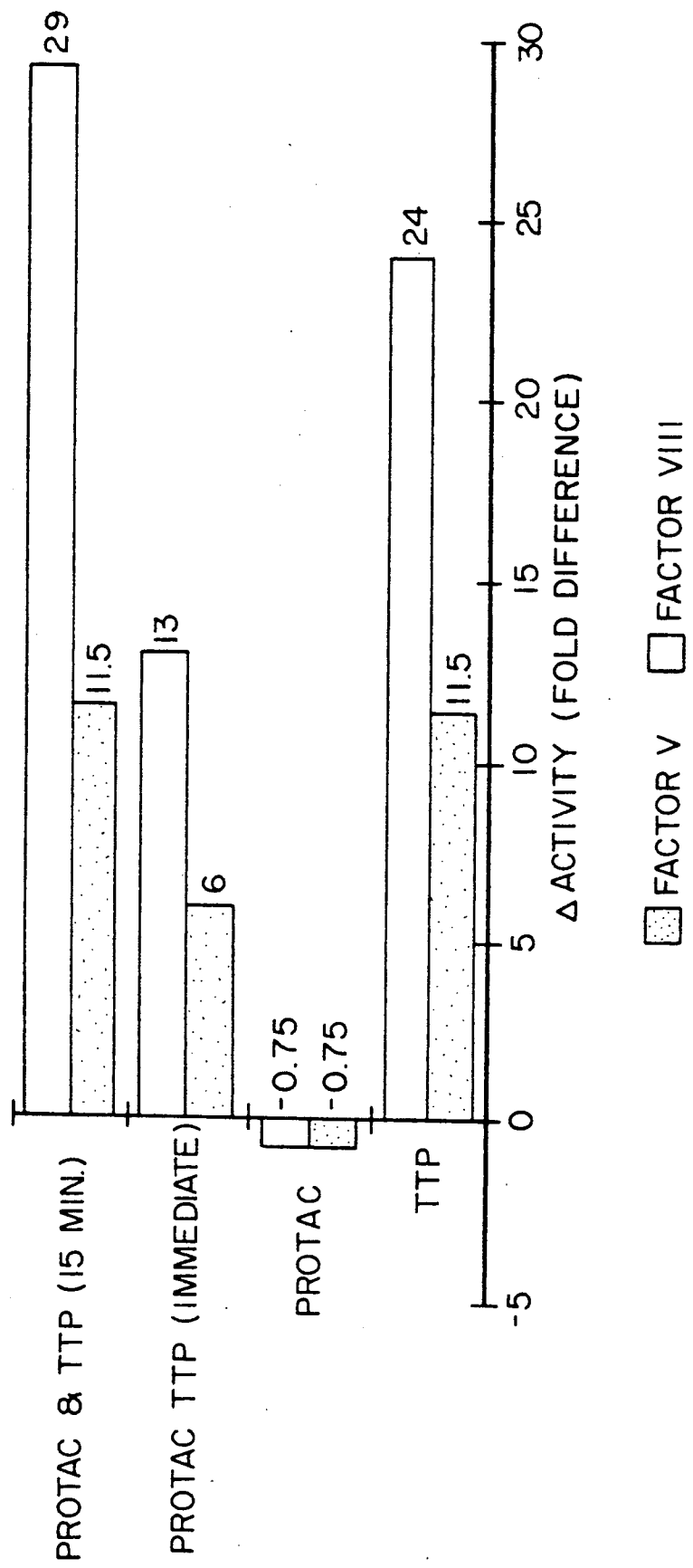

It appears from these results that PACC shares broad substrate specificity with the protease of the venom ACC of the Akistrodon Contortrix Contortrix. To test whether PACC induced prolongation of the APTT clotting times and the apparent inactivation of Factors V, VIII, X and XII was a result of direct proteolysis of the procoagulant plasma factors or a "lupus inhibitor-like" effect on plasma, a critical experiment was performed. One milliliter of PNP was added to dried PAC exactly as performed in the previous experiment and an APTT was immediately performed. The clotting time was greater than 200 seconds. Factor V and Factor VIII activities were 3% and 1% respectively. These findings correlated with the previous ones shown in FIGS. 9 and 10. The PNP/PAC mixture was then activated with 50 ul TTP/CaCl$_2$ mixture. As can be seen in FIG. 11, Factor V and Factor VIII activities measured, as previously described, were found to increase in a time dependent manner over 15 minutes incubation. In FIG. 12, the results are expressed as a change in activity (fold difference) for Factors V and VIII. It appears very likely therefore that at the enzyme to substrate ratio as recommended by the manufacturer, the effect of PACC on the clotting time of PNP is a "lupus inhibitor-like effect", and not a Protein Ca mediated inactivation of native Factors Va and VIIIa.

EXAMPLE 2

Protein C Assay. Measurement of the Biological Activity of Protein Ca as a Function of Percent Change in Factor V and Factor VIII Activity A. Determination of Optimal conditions associated with activation and inactivation of Factors V and Factor VIII in plasma.

Several experiments were performed to determine the time course activation and inactivation of Factor V and Factor VIII in plasma.

Figure 13:
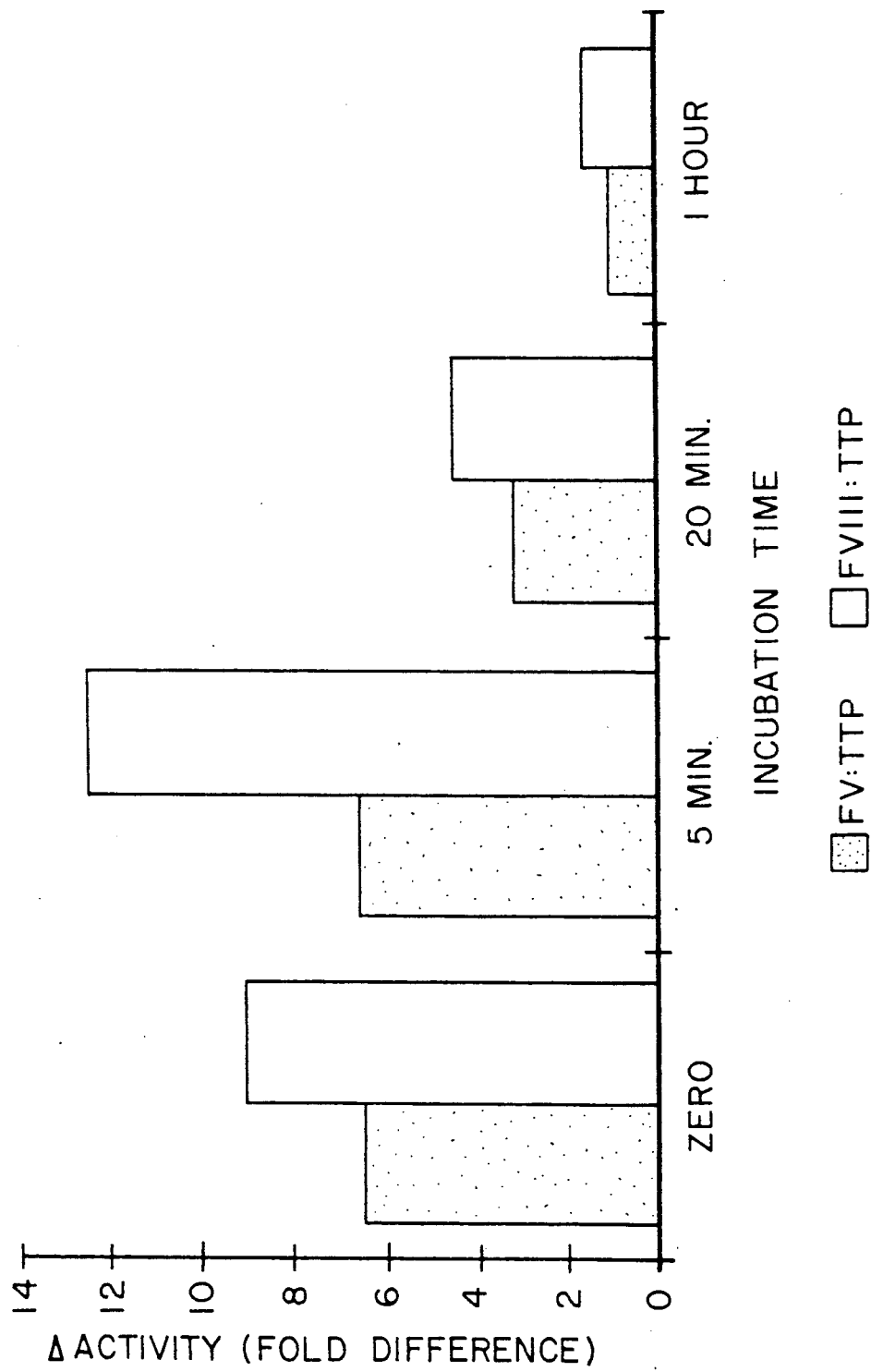
FIG. 13 is a graph showing the effect of thrombin of an APTT assay on Factors V and VIII activity.

1. Time course of thrombin mediated activation of Factor V and Factor VIII by addition of TTP/CaCl$_2$ to 1 ml PNP. In FIG. 13, the results of an experiment in which 20 ul of a 0.02M mixture of TTP/CaCl$_2$ was added to 1 ml PNP are presented. Factor V and Factor VIII activity were measured immediately following activation (zero time), then at five minutes, 20 minutes, and one hour. As can be seen, a six fold increase in Factor V activity and a nine fold increase in Factor VIII activity occurred immediately following activation. There was a further rise in Factor VIII activity (12 fold increase from initial activity) at the end of five minutes, while Factor V activity remained constant at six fold increase above baseline activity. At the end of one hour an almost complete inactivation of the activated Factor V and activated FVIII had occurred.

2. Time course effect of 100 ng ACC venom on Factor V and Factor VIII activity.

Figure 14:
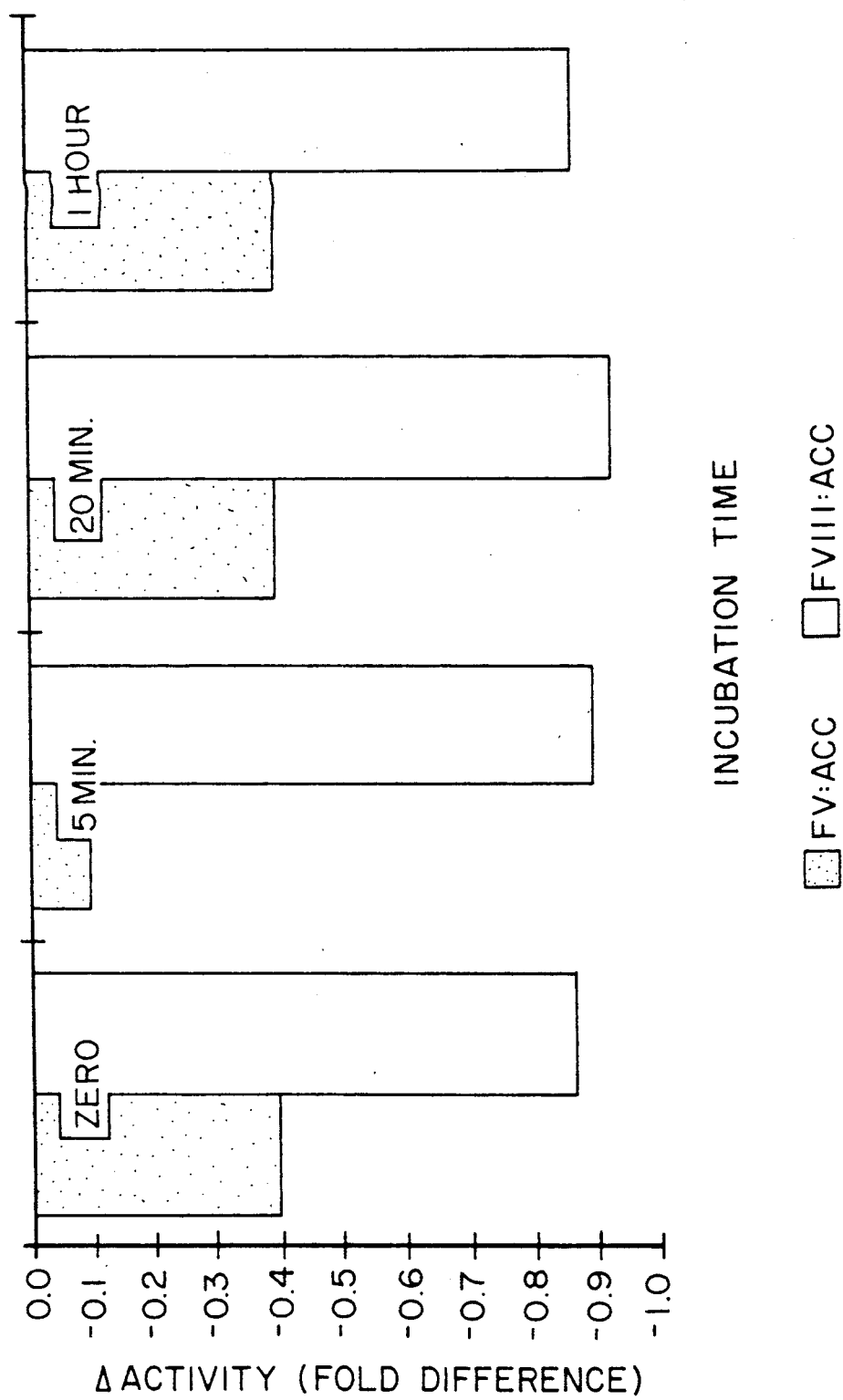
FIG. 14 is a graph showing the effect on the APTT assay of 100 ng of ACC snake venom on nonactivated Factors V and VIII.

The effect of 100 ng ACC venom on nonactivated Factor V and Factor VIII was examined in 1 ml plasma. A very mild decrease in Factor V activity at zero time from 20% to 12% (−0.4 fold) was followed by a slight rise to baseline activity (16-20%) at five minutes and a further drop to 12% (−0.4 fold) which continued until the end of the experiment (FIG. 14). There was no rise in Factor VIII activity at five minutes. The decrease in Factor VIII activity at zero time from 15 to 2.5% (−0.9 fold) was twice that of Factor V and the apparent loss in activity was maintained over the one hour duration of the experiment.

3. Time course effect of thrombin and Protein Ca mediated activation and inactivation of Factors V and VIII.

Fixed amounts of ACC venom (100 ng) and varying amounts of TTP/CaCl$_2$ were used to identify optimum activation and inactivation conditions for the thrombin/Protein Ca mediated process. In four experiments 1 ml PNP was activated first by TTP/CaCl$_2$ and, immediately following, ACC venom (100 ng) was added. Factor V and Factor VIII activities were measured in genetically deficient Factor V and FVIII plasmas as described in the materials and methods.

Figure 15:
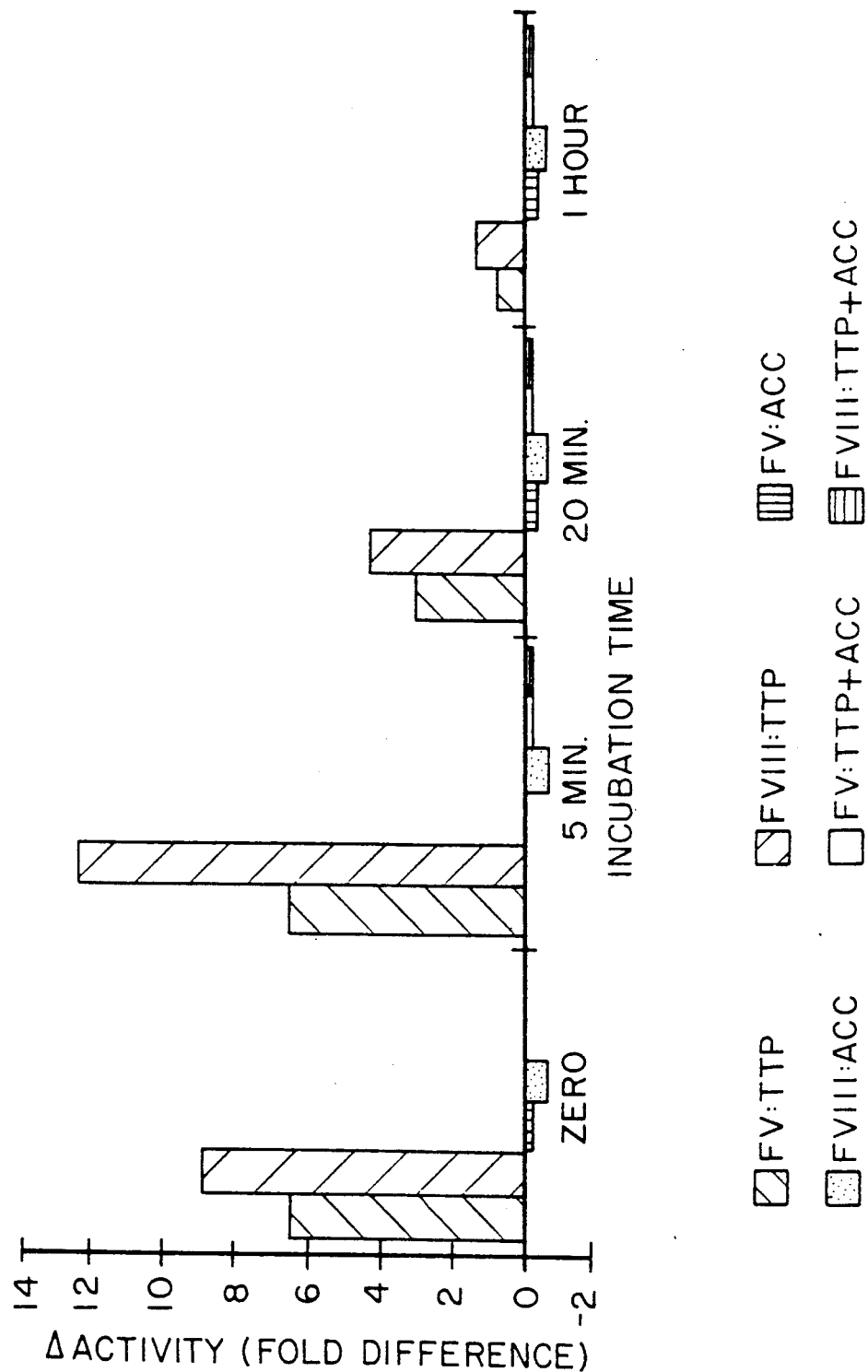
FIGS. 15 and 16 are graphs showing the effect of 100 ng of ACC snake venom and TTP (10 ul and 20 ul)-/CaCl$_2$ with activated PNP 10 ul and 20 ul.
Figure 16:
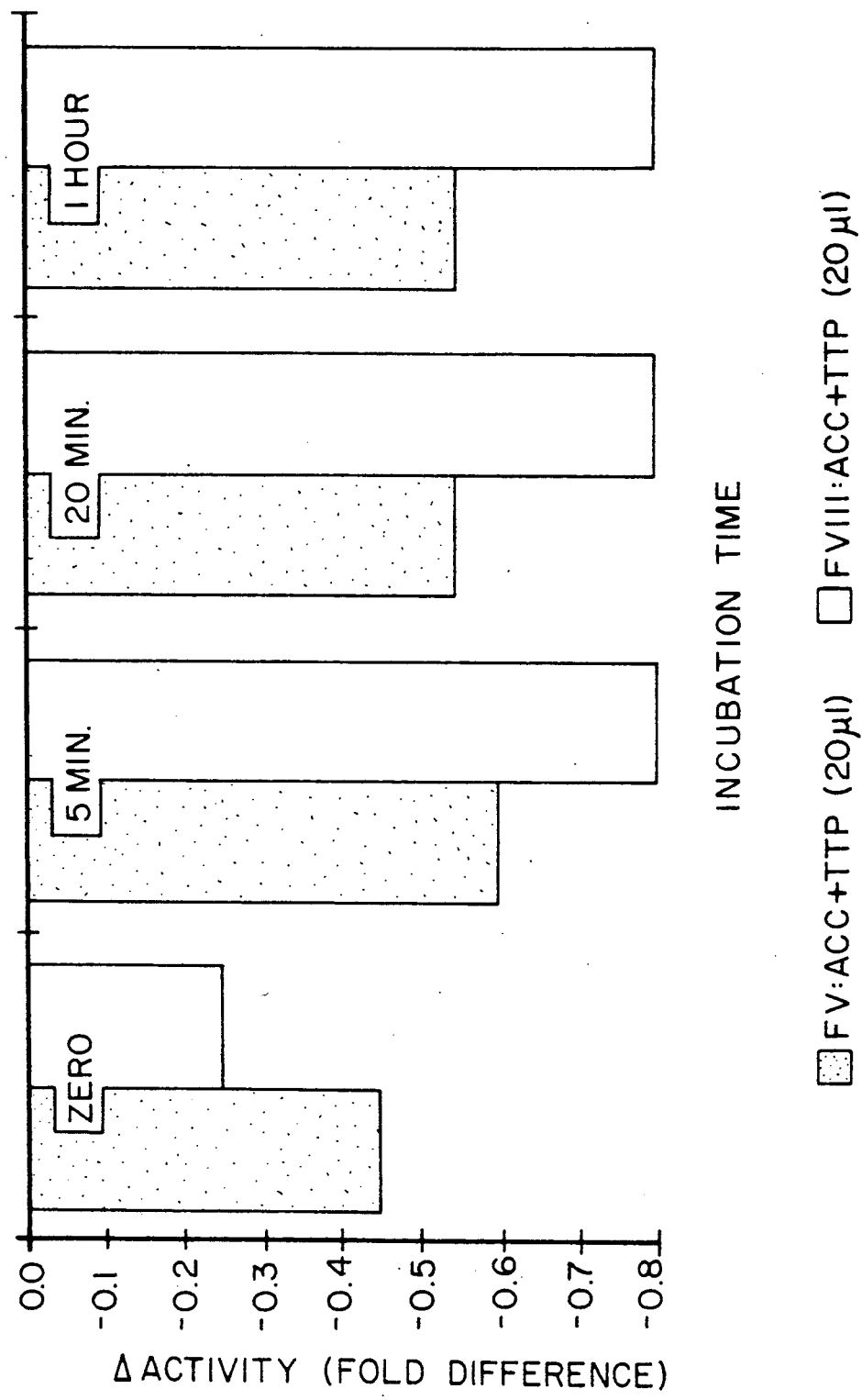

The effect of TTP/CaCl$_2$ (10 ul and 20 ul) on Factor V and Factor VIII activation and inactivation in the presence of ACC venom was not significant. This is demonstrated in FIGS. 15 and 16.

Figure 17:
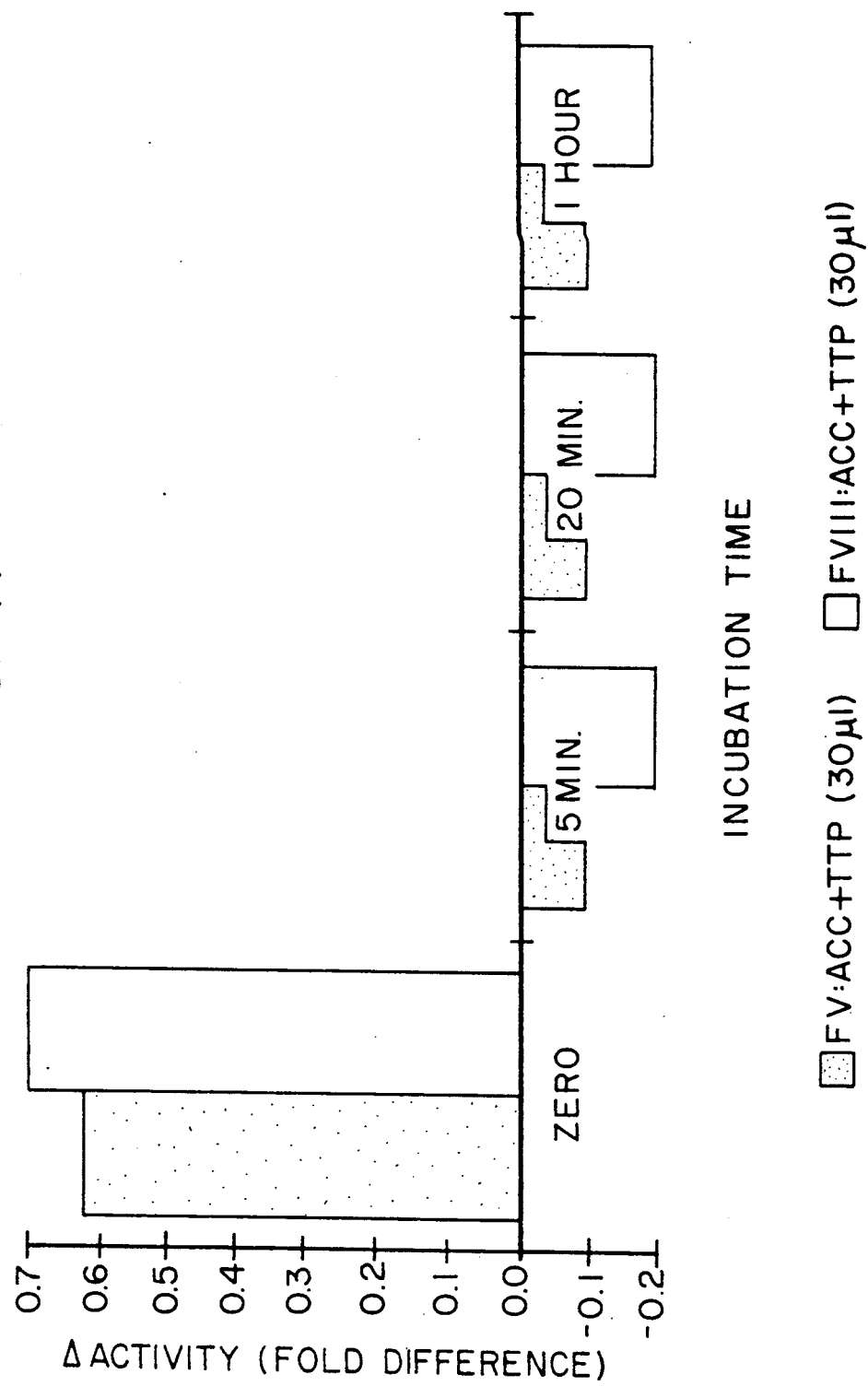
FIGS. 17 and 18 are graphs showing the results of an APTT assay and the effect of thrombin and ACC snake venom on Factor V and VIII activity at 30 ul of TTP and 50 ul of TTP.
Figure 18:
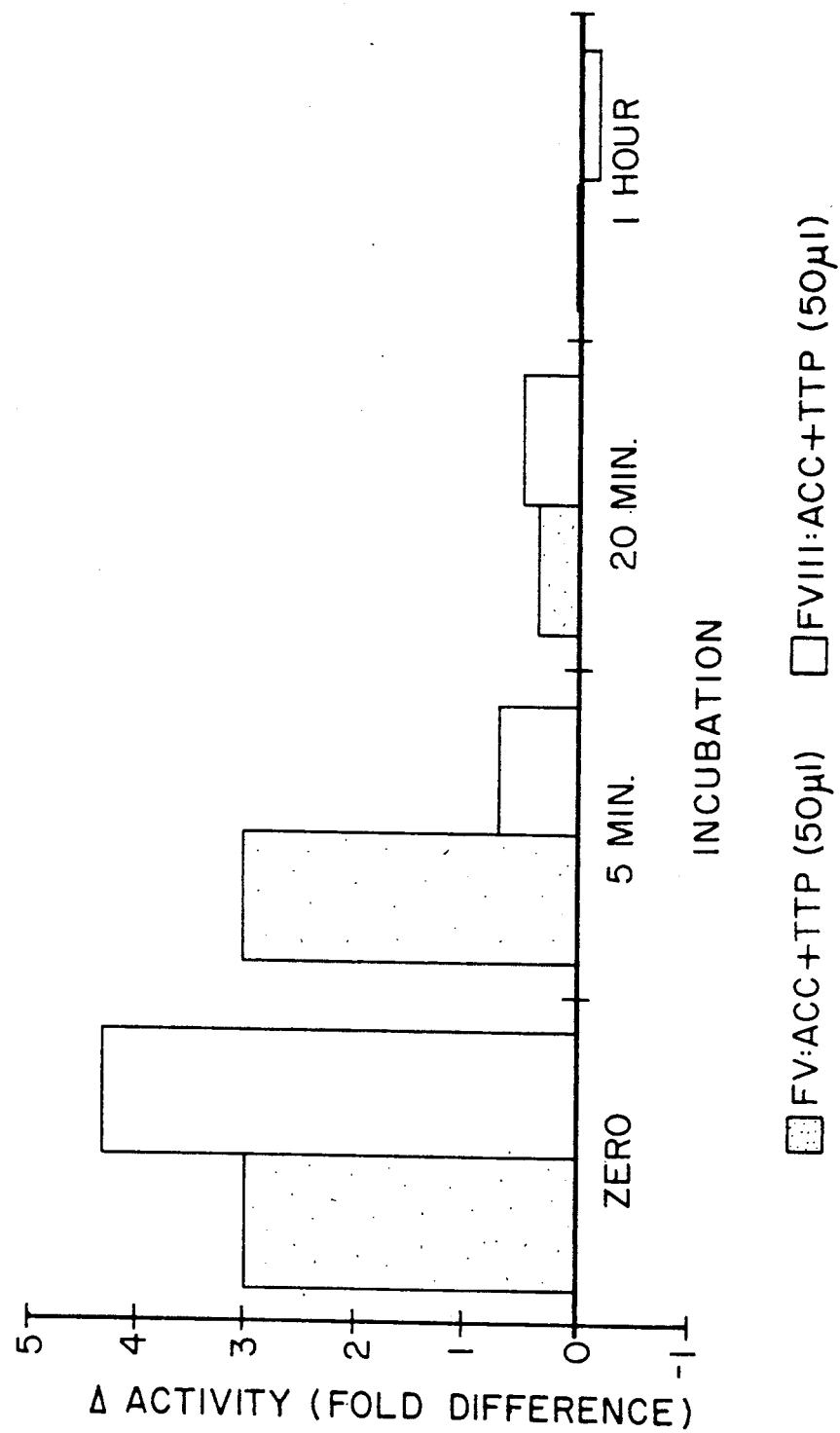

The effect of TTP/CaCl$_2$ (30 ul and 50 ul) can be seen in FIGS. 17 and 18. There is an immediate three fold increase in Factor V activity and a four fold increase in Factor VIII activity. After five minutes Factor VIII activity is almost gone while Factor V activity remains constant. At 20 minutes Factor V and Factor VIII activities have reached preactivation levels.

Figure 19:
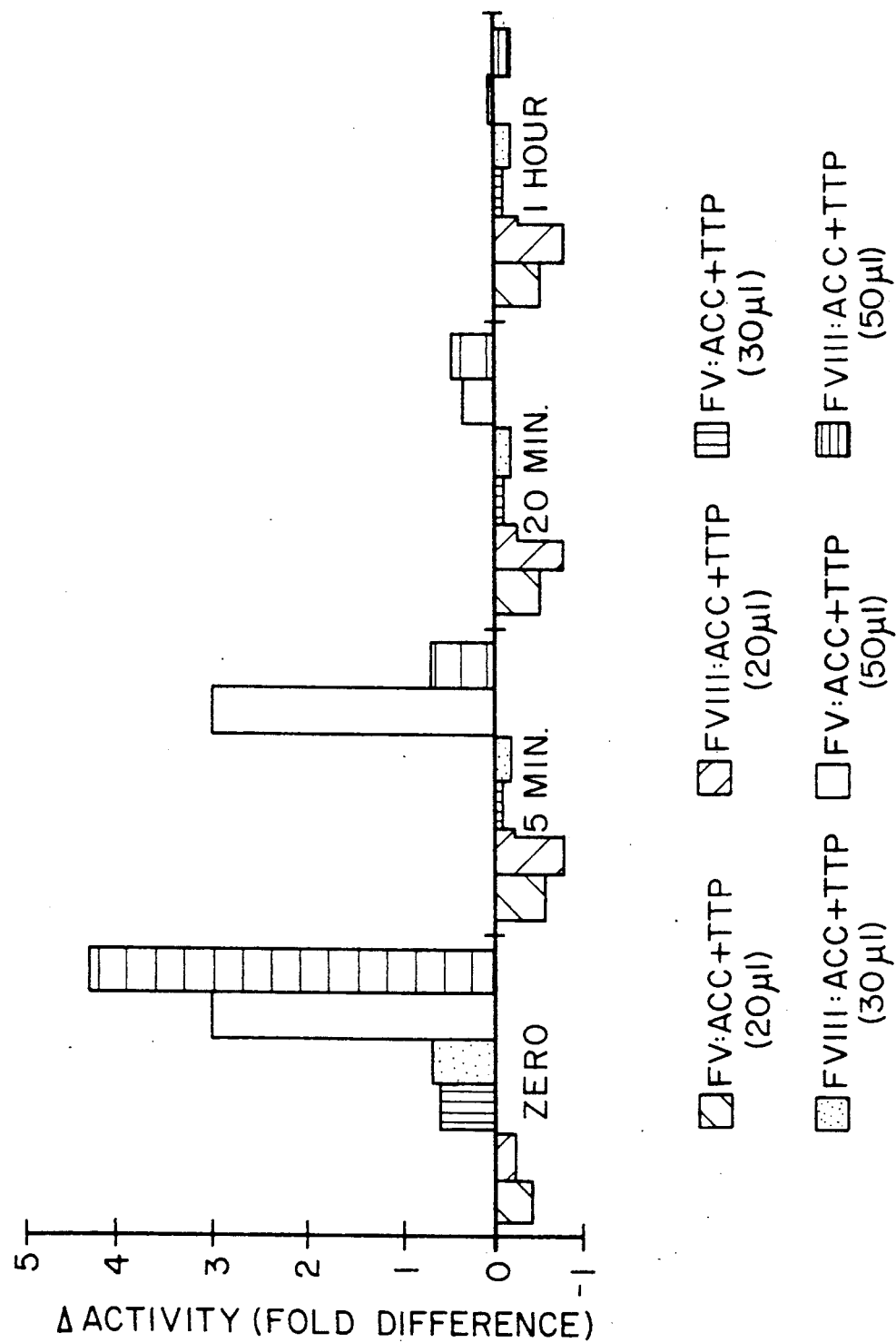
FIG. 19 is a graph showing the results of an APTT assay at various concentrations of TTP/CaCl$_2$ and 100 ng of ACC snake venom.

A graph comparing results from all the experiments is presented in FIG. 19. Optimal activation and inactivation of Factor V and Factor VIII appears to be associated with 50 ul TTP/CaCl$_2$ and 100 ng Akistrodon Contortrix Contortrix venom.

B. Standard Curves for Protein C Activity

The source of Protein C was PNP in concentrations of 20% (600 ul), 40% (1.2 ml), 50% (1.5 ml), 66.7% (2 ml), 73.3% (2.2 ml), and 80% (2.7 ml) added to Protein C deficient plasma to achieve a total volume of 3 ml.

Three types of Protein C deficient plasmas were used to construct the standard curves.

1. Protein C deficient freeze dried plasma reagent purchased from Diagnostica Stago, Asnieres, France.

2. PNP immunodepleted by insolubilized anti-Protein C antibodies raised in rabbits (as described in materials and methods)

3. Plasma obtained from a patient poisoned with a coumarin derivative used to exterminate rodents.

The Protein C assay was performed as follows: to the 1 ml plasma mixtures (deficient plasma and PNP) was added TTP/CaCl$_2$ (30 ul) and ACC venom (100 ng). Factor V and Factor VIII measurements before activation, after activation with TTP/CaCl$_2$ and after incubation with TTP/CaCl$_2$ and ACC venom for 30 minutes were performed as previously described.

The clotting times by PT and APTT for the three types of Protein C deficient plasmas are presented in Table III.

TABLE III

| Protein C Deficient Plasma | PT CT (sec.) Cont. = 11.2 | APTT CT (sec.) Cont. = 26.4 |
|---|---|---|
| Diagnostica Stago | 16.5 | 57.1 |
| Immunodepleted | 12.8 | 33.9 |
| Coumarinized | 72.0 | 132.4 |

Factor V and Factor VIII activity levels were determined in all three deficient plasma types before activation, after activation with TTP/CaCl$_2$, and after activation with TTP/CaCl$_2$ and ACC venom. The results are presented in Table IV.

TABLE IV

| Protein C Deficient Plasma Type | Before Activation Activity | | After Activation TTP/CaCl$_2$ (30 μl) Activity | | After Activation TTP/CaCl$_2$ (30 μl) ACC (100 ng) 30 mins. Incubation Activity | |
|---|---|---|---|---|---|---|
| | FV | FVIII | FV | FVIII | FV | FVIII |
| Diagnostica Stago | 4% | 4% | 100% | 100% | 100% | 100% |
| Immunodepleted | 16–20% | 16–20% | 100% | 100% | 100% | 100% |
| Coumarinized | 8% | 2% | 24% | 80% | 14% (10% decrease) | 8% (72% decrease) |

As can be seen from the results, there is no detectable Protein Ca mediated inactivation of Factor Va or Factor VIIIa in the Protein C deficient plasmas from Diagnostica Stago and the immunodepleted plasma. In the coumarinized plasma a substantial decrease in Factor VIII activity from 70% to 8% is observed while the decrease in Factor V activity is more modest from 24% down to 14%. The modest drop in Factor V activity as compared to the substantial decrease in Factor VIII activity could be attributed to the effect of the coumarin derivative on a post translational vitamin K-dependent process necessary for the biological activity of Protein S as well as Protein C. Protein S has been shown to have an independent role in the regulation of Protein Ca mediated inactivation of Factor Va.

To construct standard curves, Protein deficient plasma/PNP mixtures (1 ml) were activated with TTP/CaCl$_2$ (30 ul) and ACC venom (100 ng). At the end of 30 minutes incubation at 37° C., the plasma mixtures (30 ul) were added to 70 ul of Factor V or Factor VIII deficient plasma and APTT assays were performed as described in the materials and methods section. The patterns of inactivation for Factor V and for Factor VIII by Protein Ca were identical in Diagnostica Stago Protein C deficient plasma or immunodepleted plasma. These results are seen in Table V and are graphically represented in FIG. 20.

TABLE V

Inactivation of Factor Va and Factor VIIIa by Protein Ca-Standard Curve of Actual Data Points

| Factor Va | | Factor VIIIa | |
|---|---|---|---|
| Protein C Activity | FVa Inactivated | Protein C Activity | FVIIIa Inactivated |
| 20–40% | 70% | 20% | 60% |
| 50–66.7% | 88% | 40–66.7% | 80% |
| 73.3–80% | 92% | 73% | 92% |
| | Slope = .417 | 80% | 98.5% |
| | 4 = .9029 | | Slope = .540 |
| | Y int. = 60.38 | | r = .925 |
| | | | Y int. = 51.8 |

In Table V and VII the percent inactivation of Factor Va and Factor VIIIa activities by protein Ca were derived from the straight lines of the best fit of the actual data points.

TABLE VI

Inactivation of Factor Va and Facor VIIIa by Protein Ca-Standard Curve of Inactivation Derived From the Straight Lines of Best Fit

| Factor Va | | Factor VIIIa | |
|---|---|---|---|
| Protein C Activity | FVa Inactivated | Protein C Activity | FVIIIa Inactivated |
| 20% | 68.7% | 20% | 62.7% |
| 40% | 77% | 40% | 73.5% |
| 50% | 81.2% | 50% | 78.9% |
| 66.7% | 88.2% | 66.7% | 87.9% |
| 73.3% | 90.9% | 73.3% | 91.5% |
| 80% | 93.8% | 80% | 95.1% |
| From Actual Data Points | Slope = .417 r = .9029 Y int. = 60.38 | From Actual Data Points | Slope = .540 r = .925 Y int. = 51.8 |

TABLE VII

Protein Ca Mediated Inactivation of Factor Va and Factor VIIIa

| Protein C Activity | FVa Inactivated | FVIIIa Inactivated |
|---|---|---|
| 20% | 68.67% | 62.66% |
| 30% | 72.85% | 68.0% |
| 40% | 77.0% | 73.48% |
| 50% | 81.20% | 78.80% |
| 60% | 85.38% | 84.30% |
| 65% | 87.41% | 86.99% |
| 70% | 89.56% | 89.70% |
| 75% | 91.65% | 92.40% |
| 80% | 93.74% | 95.10% |
| 85% | 95.83% | 97.80% |
| 90% | 97.90% | 100% |
| 95% | 100% | |

Figure 20:
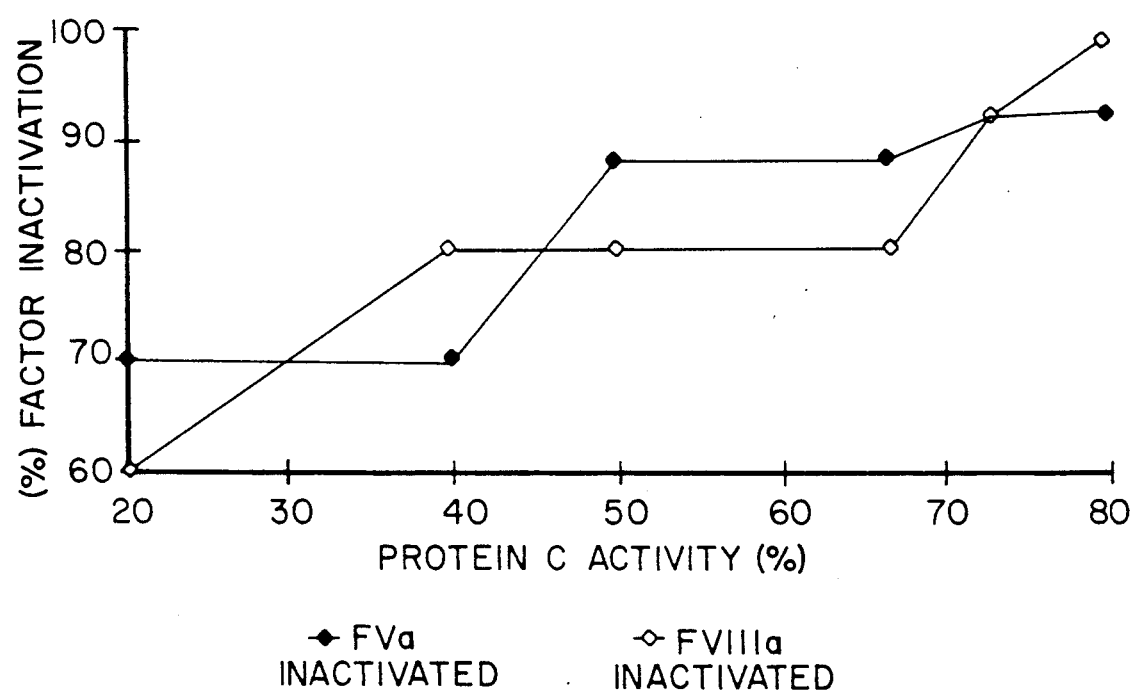
FIG. 20 is a graph showing a standard curve for Protein Ca activating as a function of Factors Va and VIIIa inactivation.
Figure 21:
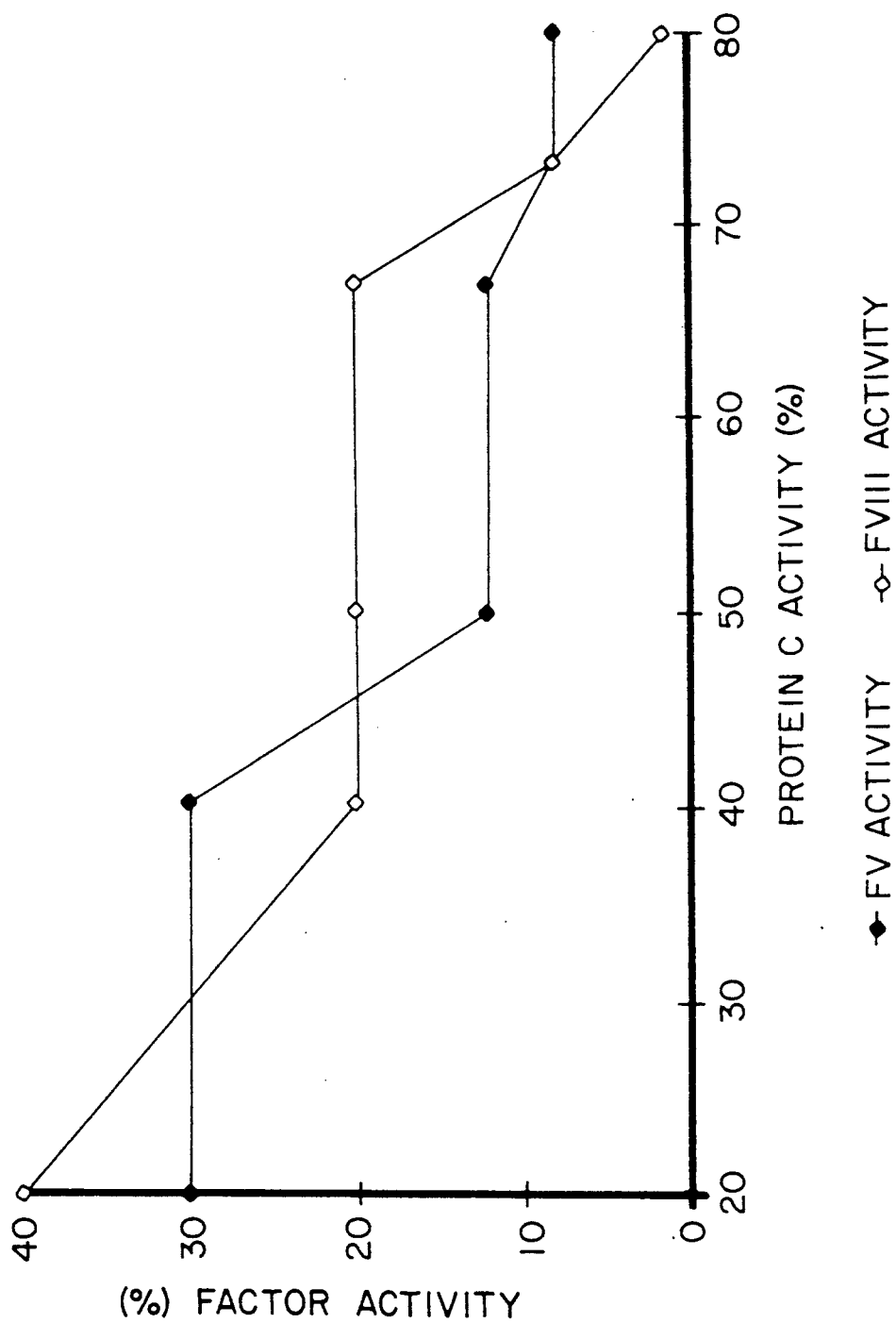
FIG. 21 is a graph showing the percent factor activity as a function of Protein C activity.

A standard curve showing actual data points and the line of the best fit are expressed graphically in FIG. 20 for Factor Va inactivation and in FIG. 21 for Factor VIIIa inactivation by Protein Ca.

Figure 22:
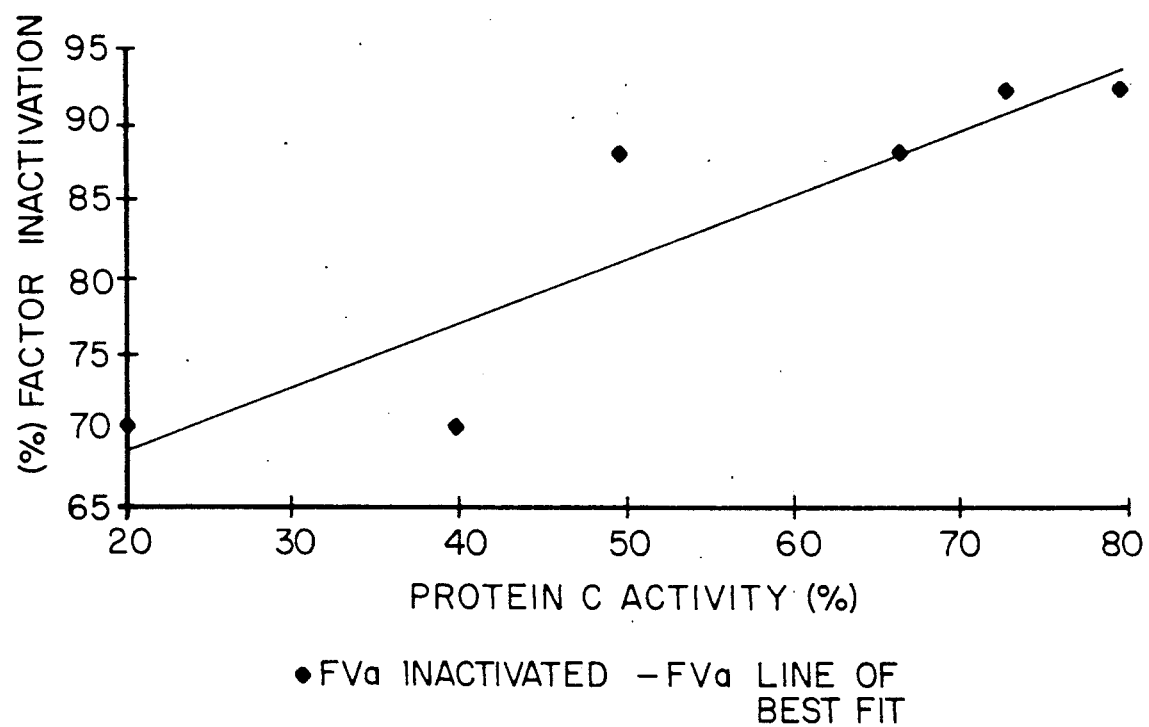
FIG. 22 is a graph showing the percent Factor inactivation of Factor Va as a function of Protein C activity.
Figure 23:
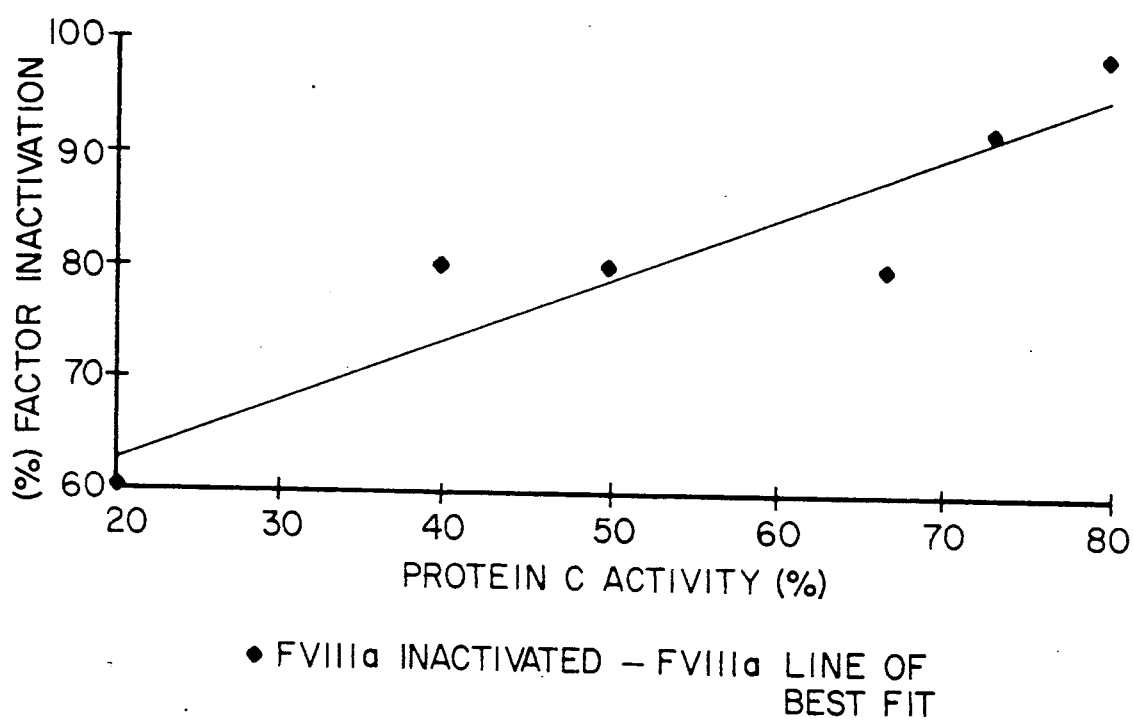
FIG. 23 is a graph showing the percent inactivation of Factor VIIIa as a function of Protein C activity.

The residual Factor Va and Factor VIIIa activity as a function of the Protein Ca mediated inactivation process are shown in FIGS. 22 and 23.

Two computer derived compilations of the possible permutations for Factor V activity (Table VIII) and Factor VIII activity (Table IX) as a function of the clotting times by the APTT assay were developed to aid in the determination of Protein Ca mediated inactivation of Factor Va and Factor VIIIa.

TABLE VIII

FACTOR V - ACTIVITY

| APTT (secs.) | % FV activity | APTT (secs.) after act. SD+ | FV activity after activation | Δ activity | fold change |
|---|---|---|---|---|---|
| 34± secs. | 20 to 25% | 26 | 100% | 75-80% | 3.75-3 |
| | | 30 | 40% | 15-20% | 2.6-1.6 |
| | | 34 | 20-25% | 0% | 0 |
| 37± secs. | 16 to 20% | 26 | 100% | 80% | 4 |
| | | 30 | 40% | 20% | 2.5-2 |
| | | 34 | 25% | 19-5% | 1.6-1.25 |
| 42 to 47 secs. | 8 to 12% | 26 | 100% | 88% | 7.5 |
| | | 30 | 40% | 28% | 3.5 |
| | | 34 | 25% | 13% | 2 |
| | | 37 | 16-20% | 4-8% | 0.16 |
| | | 42 | 8-12% | 0% | 0 |
| 53 secs. | 4% | 26 | 100% | 96% | 24 |
| | | 30 | 40% | 36% | 10 |
| | | 34 | 25% | 21% | 6.25 |
| | | 37 | 16-20% | 12-16% | 4-5 |
| | | 42 | 8-12% | 4-8% | 2-3 |
| | | 53 | 4% | 0 | 0 |
| 65 to 90 secs. | 1 to 2% | 26 | 100% | 98-99% | 50-100 |
| | | 30 | 40% | 38-39% | 19-40 |
| | | 34 | 25% | 23-24% | 12-24 |
| | | 37 | 16-20% | 15-19% | 10-20 |
| | | 42 | 8-12% | 7-11% | 4-6 |
| | | 53 | 4% | 2-3% | 2-4 |
| | | 65-90 | 1-2% | 0 | 0 |

TABLE IX

FACTOR VIII - ACTIVITY

| APTT (secs.) | % FV activity | APPT (secs.) after act. SD+ | FVIII activity after activation | Δ activity | fold change |
|---|---|---|---|---|---|
| 33 ± 1 secs. | 20 to 25% | 26 | 100% | 75-80% | 3.75-3 |
| | | 30 | 40% | 15-20% | 2.6-1.6 |
| | | 34 | 20-25% | 0% | 0 |
| 37 secs. | 12% | 26 | 100% | 88% | 7 |
| | | 30 | 40% | 28% | 3.4 |
| | | 34 | 25% | 8-12% | 1.6-2 |
| | | 37 | 12% | 0 | 0 |
| 42 secs. | 8% | 26 | 100% | 92% | 12.5 |
| | | 30 | 40% | 32% | 5 |
| | | 34 | 25% | 12-17% | 2.5-3 |
| | | 37 | 12% | 4% | 1.5 |
| | | 42 | 8% | 0 | 0 |
| 46 to 48 secs. | 2 to 4% | 26 | 100% | 98-96% | 49-24 |
| | | 30 | 40% | 38-36% | 19-9.5 |
| | | 34 | 25% | 18-21% | 9-5 |
| | | 37 | 12% | 10-8% | 5-2 |
| | | 42 | 8% | 6-4% | 3-0 |
| 55 to 80 secs. | 1.5 to less than 1% | 26 | 100% | 98.5% | 65 |
| | | 30 | 40% | 38.5% | 25 |
| | | 34 | 25% | 18.5-23.5% | 12-16 |
| | | 37 | 12% | 10.5% | 7 |
| | | 42 | 8% | 6.5% | 4.3 |
| | | 46-48 | 2-4% | 0.5-2.5% | 2 |
| | | 55-80 | 1.5-<1% | 0 | 0 |

Data is presented for Factor V and Factor VIII before activation, and after the thrombin introduced change in native Factor V to Factor Va and in native Factor VIII to Factor VIIIa. As mentioned earlier, thrombin is generated in plasma by adding small quantities of $TTP/CaCl_2$ (20 ul, 30 ul, 50 ul) that are not sufficient to induce fibrin formation, but enough to cause several fold enhancement of Factor V and Factor VIII activity. The percent change in activity at each level and the fold change in activity from non-activated to activated state are also shown in the Tables. The changes in Factor V and Factor VIII activity have been calculated for plasma levels of these factors ranging from 25% to less than 1%. This makes possible the use of the tables with a wide range of plasma types from healthy or diseased individuals. Oral anticoagulant therapy does not cause decreases in Factor V or Factor VIII activities in plasma, however, generation of thrombin by $TTP/CaCl_2$ in plasmas from coumadinized individuals is a function of the levels of biologically active Factors VII, IX, X and prothrombin. In heavily coumadinized plasmas very little thrombin is generated and thus activation of Factor V and Factor VIII is incomplete. Similarly in liver disease and even in aged plasma or in the presence of a lupus inhibitor the activation process is more subtle than in PNP. This may also be true for hypercoagulable disease and DIC.

Thus, by the use of Tables VIII and IX it is possible to determine the Protein Ca mediated decrease in Factor Va and Factor VIIIa activity that indirectly reflects Protein C biological activity.

As can be seen from the standard curves and from the coumarinized patient's plasma, very little Protein Ca (20%) is needed to inactivate about ⅔ of activated Factor Va (70%) and Factor VIIIa (60%).

Protein C mediated inactivation of Factor V and Factor VIII was examined in plasmas from several patients administered therapeutic doses of heparin for thrombosis related problems. These results can be seen in Table X.

TABLE X

Effect of Heparin Therapy on Factor V and Factor VIII activity

| | Factor V Activity | | | Factor VIII Activity | | |
|---|---|---|---|---|---|---|
| Patient Name | Before Activation (Control: 20%) | After Activation (Control: 100%) | Snake Venom (Control: 1-20%) | Before Activation (Control: 20%) | After Activation (Control: 10%) | Snake Venom (Control: 1-20%) |
| N.M. | 3% | 8% | 2% | 4% | 10% | 1.5% |
| S.T. | 5% | 14% | 5% | 10% | 100% | 25% |
| N.W. | 1.5% | 15% | 1.5% | 2% | 12% | 1% |
| S.B. | 1.5% | 2% | 1.5% | 1.5% | 2% | 1.5% |
| K.D. | 2% | 16% | 2% | 1.5% | 30% | 2% |

In a very recent publication (Antithrombin III-dependent Antiprothrombinase Activity of Heparin and Heparin Fragments", Schoen, P., et al., J. Biol Chem 264:100002-7, 1989). Schoen et al hypothesize that the formation of the dissociable ternary ATIII-heparin-Factor Xa complex results in a (partial) loss of Factor Xa activity towards its natural substrate, prothrombin. Thus, the activation of Factor V and Factor VIII is decreased in heparinized plasma as a result of a decrease in the initial rate of thrombin generation in the presence of ATIII.

Also studied was Factor Va and Factor VIIIa inactivation in the case of a 33 year old patient on continuous heparin therapy for almost three years with spontaneous recurrent DVT and cavenous sinus thrombosis while on heparin. In this patient, Factor V and Factor VIII activity remained high and was not inactivated by Protein Ca. However, Protein C immunoreactive levels as well as Protein C purified from the patient's plasma were found in Dr. Miletich's laboratory to be normal. An explanation for the persistence of activated Factor V and Factor VIII in plasma and the recurrence of thrombosis while on heparin therapy is explained in a recent publication. Pratt et al purified Protein C inhibitor and studied the effect of heparin on purified Protein C inhibitor interaction with proteases. A heparin-dependent inhibition of activated Protein C was demonstrated that indicates a "procoagulant effect of heparin" mediated via Protein C inhibitor (Protein C Inhibitor: Purification and Proteinase Reactivity, Pratt, C. W., et al., Thrombos Res 53: 595-602, (1989)).

The mechanism for thrombosis in heparinized patients could, therefore, be the result of circulating activated Factor V and Factor VIII procoagulant activities. Under challenge to the hemostatic system, such as a decrease in the blood flow, activated Factor V and Factor VIII would increase the initial rate of thrombin generation. Thus, the hypothesis of an immediate irreversible heparin-dependent inactivation of the 33 year old patient's Protein Ca could be the likely cause of his recurrent thrombotic problems that started at age 23. This hypothesis remains to be confirmed.

An assay that measures the activation and inactivation of Factor V and Factor VIII in plasma is a sensitive indicator for hypercoagulability and reflects an imbalance of more than just the Protein C inhibitor pathway.

It is intended that the foregoing description be only illustrative of the present invention and that the present invention be limited only by the hereinafter appended claims.

I claim:

1. A method for diagnosing a thrombic disease by testing for inactivation of Factors Va and VIIIa by activated Protein C (Protein Ca) which comprises:
    (a) activating Factor V and Factor VIII to Factor Va and Factor VIIIa and activating Protein C to Protein Ca in separate containers of patient plasma and pooled normal plasma (PNP) without fibrin formation in the plasmas;
    (b) allowing time for Protein Ca to inactivate Factor Va and Factor VIIIa in each of the containers; and
    (c) determining a clotting time of the patient plasma and the PNP in each container using an activated thromboplastin assay (APTT) wherein a patient plasma with a decreased APTT over the PNP has an indication of thrombic disease.

2. A method for indirectly assaying for Protein C in blood plasma which comprises:
    (a) activating Factor V and Factor VIII to Factor Va and Factor VIIIa and activating Protein C to activated Protein C (Protein Ca) in separate containers of pooled normal plasma (PNP) and patient plasma without fiber formation in the plasmas;
    (b) allowing time for Protein Ca to inactivate Factor Va and Factor VIIIa in each of the containers; and
    (c) determining a clotting time of the patient plasma and the PNP in each container using an activated thromboplastin time assay (APTT) of the PNP and the patient plasma in each container, wherein a particular patient plasma with a deficiency of protein C or with increased inhibitor activity against Protein Ca has a decreased APTT compared to the APTT of PNP.

3. The method of claim 2 wherein a Protein C activation accelerator is added to the plasmas in step (a).

4. A method for indirectly assaying for Protein C in blood plasma which comprises:
    (a) activating Factor V and Factor VIII to Factor Va and Factor VIIIa and activating Protein C to activated Protein C (Protein Ca) in separate containers of a pooled normal plasma (PNP) and of a patient plasma without fibrin formation in the plasmas; and
    (b) measuring inactivation of Factor Va and Factor VIIIa for Protein Ca in the patient plasma and in the PNP by an activated partial thromboplastin time assay (APPT).

5. The method of claim 4 wherein the activation of Protein C to Protein Ca is accelerated by an activation accelerator.

6. A method for indirectly assaying for Protein C in blood plasma by activating Factor V to Factor Va and Factor VIII to Factor VIIIa and Protein C to activated Protein C (Protein Ca) in the plasma which comprises:
    (a) providing separate containers of patient plasma and pooled normal plasma (PNP);
    (b) adding thrombomodulin tissue factor (TTP) and calcium chloride to the plasmas in each container so as to activate Factor V to Factor Va, Factor VIII to Factor VIIIa and Protein C to Protein Ca without fibrin formation in the plasmas;
    (c) allowing time for Protein Ca to inactivate Factor Va and Factor VIIIa formed by the addition of the TTP and the calcium chloride to the plasmas; and
    (d) determining a clotting time of the patient plasma and the PNP in each container using an activated thromboplastin assay (APTT), wherein a particular patient plasma with a deficiency of Protein C or increased inhibitor activity to Protein Ca has a decreased APTT compared to the APTT of PNP.

7. The method of claim 6 wherein a Protein C activation accelerator is added to the plasmas in each container in step (b).

8. A method for indirectly assaying for Protein C by activating Factor V to Factor Va and Factor VIII to Factor VIIIa and Protein C to Protein Ca in blood plasma which comprises:
    (a) providing in separate containers patient plasma and control pooled normal plasma (PNP);
    (b) adding thrombomodulin tissue factor (TTP) and calcium chloride to the plasmas in each container so as to activate Factor V to Factor Va and Factor VIII to Factor VIIIa and Protein C to Protein Ca without fibrin formation in the plasmas;
    (c) separately mixing Factor VIII and Factor V deficient plasmas with an aliquot of the PNP and with an aliquot of the patient plasma from each of the containers so that the PNP and patient plasma can correct the deficiency of the deficient plasmas if the Factor V and the Factor VIII are normal in the patient plasma;

(d) allowing time for Factor V and Factor VIII to be activated to Factor Va and Factor VIIIa and then to be inactivated by Protein Ca in the separate containers containing the mixtures with the deficient plasmas; and (e) determining a clotting time of the patient plasma and the PNP in each container containing the mixtures with the deficient plasmas using an activated thromboplastin time assay (APTT), wherein a patient plasma with a deficiency of Protein C or an increased inhibitor to Protein C activity has a decreased APTT compared to the APTT of PNP.

9. The method of claim 8 wherein a Protein C activation accelerator is added to the plasmas in each container in step (b).

10. The method of claim 8 wherein snake venom is admixed with the plasmas in step (b) to accelerate the activation of Protein C to Protein Ca.

11. The method of claim 10 wherein the snake venom is Akistrodon Contortrix Contortrix venom or an active component thereof.

12. The method of claim 8 wherein the TTP and calcium chloride as a reagent produces a selected standardizing prothrombin time (PT) in PNP of between about 10 and 13 seconds.

13. The method of claim 12 wherein the time is about 11.6 seconds ±0.5 second.

14. The method of claim 13 wherein Akistrodon contortrix contortrix venom is admixed with the plasmas in step (b) to accelerate the activation of Protein C to Protein Ca.

15. The method of claim 8 wherein in step (c) 30 parts by volume of PNP and patient plasma are separately mixed with 70 parts by volume each of Factor V and Factor VIII deficient plasma.

16. The method of claim 15 wherein the APTT is determined by adding an APTT reagent to the plasmas in each container and then adding calcium chloride to clot the plasma in each container.

17. The method of claim 16 wherein the APTT reagent produces a selected clotting time of between about 20 and 30 seconds in PNP with a mean range of about 26 seconds for greater than two thirds of individuals with normal plasma.

18. The method of claim 8 wherein in addition a control plasma depleted of Protein C is tested along with the PNP and patient plasma.

19. The method of claim 8 wherein in addition a control plasma with a known amount of Protein C is tested along with the PNP and patient plasma.

20. The method of claim 8 wherein the TTP produces a selected standardized prothrombin time (PT) between about 10 and 13 seconds and wherein the TTP is used in step (b) in an amount between 20 and 50 microliters per milliliter of patient plasma and PNP to generate thrombin without formation of fibrin.

21. The method of claim 20 wherein the TTP is added in 10, 20, 30 and 50 milliliter amounts to separate containers of PNP and of patient plasma in step (b).

22. The method of claim 8 wherein the time in step (d) is between about 0.5 and 24 hours.

23. The method of claim 8 wherein a Protein C activator is provided in step (b) and wherein the time in step (d) is about 1.0 hour.

24. A kit for indirectly assaying for Protein C in blood plasma by a method which comprises providing in separate containers patient plasma and control pooled normal plasma (PNP); adding thrombomodulin/tissue factor (TTP) and calcium chloride to the plasmas in each container so as to activate Factor V to Factor Va and Factor VIII to Factor VIIIa and protein C to activated protein C (Protein Ca) without fibrin formation in the plasmas; separately mixing Factor VIII and Factor V deficient plasma with the activated PNP and with the activated patient plasma in each of the containers; allowing time for Factor VIII and Factor V to be activated to Factor Va and Factor VIIIa and then the Factors Va and VIIIa to be inactivated by Protein Ca in the separate containers; and determining a clotting time of the patient plasma and the PNP in each container using an activated thromboplastin time assay (APTT), wherein a patient plasma with a deficiency of Protein C or with increased inhibitor activity against Protein Ca has a decreased APTT compared to the APTT of PNP which comprises:

(a) TTP with a standardized prothrombin time in PNP of between about 10 and 13 seconds to produce thrombin in a dosage amount of less than a dosage amount which produces fibrin formation in the PNP and the patient plasma;

(b) Factor V and Factor VIII and Protein C deficient plasmas; and (c) an APTT reagent.

* * * * *

UNITED STATES PATENT AND TRADEMARK OFFICE
CERTIFICATE OF CORRECTION

PATENT NO. : 5,051,357
DATED : September 24, 1991
INVENTOR(S) : Houria I. Hassouna It is certified that error appears in the above—identified patent and that said Letters Patent is hereby corrected as shown below:

Column 4, line 17, "FVIII to Factor VIIIa" should read --Factor VIII to Factor VIIIa--.

Column 5, line 6 "70% Factor V activity" should read --70% Factor Va activity--.

Column 5, line 15, a quotation mark -- " -- should be inserted before "Antithrombin".

Column 5, line 30, "cavenous" should be --cavernous--.

Column 7, lines 64 and 65 "Laboratoraies" should be --Laboratories--.

Column 11, line 3, "Factors VA" should read --Factors Va--.

Column 14, line 30, "Facor" should read --Factor--.

UNITED STATES PATENT AND TRADEMARK OFFICE
CERTIFICATE OF CORRECTION

PATENT NO. : 5,051,357
DATED : September 24, 1991
INVENTOR(S) : Houria I. Hassouna It is certified that error appears in the above—identified patent and that said Letters Patent is hereby corrected as shown below:

Column 15, lines 35 and 36 (Table IX), the heading "%FV activity" should read --FVIII activity--.

Column 16, lines 5 and 6 (Table IX-continued), "%FV activity" should read --FVIII activity--.

Column 16, line 65, a quotation mark -- " -- should be inserted before "Antithrombin".

Column 17, line 11, "cavenous" should be --cavernous--.

Signed and Sealed this

Sixteenth Day of February, 1993

Attest:

STEPHEN G. KUNIN

Attesting Officer     Acting Commissioner of Patents and Trademarks